United States Patent
Luo et al.

(10) Patent No.: US 10,285,668 B2
(45) Date of Patent: May 14, 2019

(54) ULTRASONIC DATA COLLECTION

(71) Applicant: Verathon Inc., Bothell, WA (US)

(72) Inventors: Si Luo, Bothell, WA (US); Joon Hwan Choi, Bothell, WA (US); Stephen Dudycha, Mercer Island, WA (US); Adam Scott Garrison, Redmond, WA (US); Craig E. Nelson, Seattle, WA (US); Matthew Caprio, Seattle, WA (US); Andrew Yum, Snohomish, WA (US)

(73) Assignee: Verathon Inc., Bothell, WA (US)

( * ) Notice: Subject to any disclaimer, the term of this patent is extended or adjusted under 35 U.S.C. 154(b) by 1104 days.

(21) Appl. No.: 14/615,245

(22) Filed: Feb. 5, 2015

(65) Prior Publication Data

US 2015/0216512 A1    Aug. 6, 2015

Related U.S. Application Data

(60) Provisional application No. 61/936,232, filed on Feb. 5, 2014.

(51) Int. Cl.
*A61B 8/00* (2006.01)
*A61B 8/08* (2006.01)

(52) U.S. Cl.
CPC .............. *A61B 8/58* (2013.01); *A61B 8/4466* (2013.01); *A61B 8/4483* (2013.01); *A61B 8/483* (2013.01); *A61B 8/5207* (2013.01); *A61B 8/5269* (2013.01); *A61B 8/56* (2013.01)

(58) Field of Classification Search
CPC combination set(s) only.
See application file for complete search history.

(56) References Cited

U.S. PATENT DOCUMENTS

| | | | |
|---|---|---|---|
| 4,476,549 A | 10/1984 | Dragonette et al. | |
| 5,485,845 A | 1/1996 | Verdonk et al. | |
| 5,538,004 A | 7/1996 | Bamber | |
| 5,699,806 A | 12/1997 | Webb et al. | |
| 5,738,099 A | 4/1998 | Chang | |
| 5,865,751 A * | 2/1999 | Okuno ................ | G10K 11/346 600/443 |
| 5,911,691 A | 6/1999 | Mochizuki et al. | |
| 5,928,151 A | 7/1999 | Hossack et al. | |
| 6,099,474 A | 8/2000 | Solek | |
| 6,132,379 A | 10/2000 | Patacsil et al. | |
| 6,139,496 A | 10/2000 | Chen et al. | |

(Continued)

FOREIGN PATENT DOCUMENTS

| | | |
|---|---|---|
| WO | 9926541 A1 | 6/1999 |
| WO | 2013098696 A1 | 7/2013 |

OTHER PUBLICATIONS

Verathon Inc., BladderScan Bladder Volume Instrument, BVI 9400 User's Manual, 2008, 80 pages, Bothell,WA.

(Continued)

*Primary Examiner* — Mohamed Charioui
(74) *Attorney, Agent, or Firm* — Snyder, Clark, Lesch & Chung, LLP

(57) ABSTRACT

Embodiments include systems and or methods directed to ultrasound calibration, real-time C-mode approaches, calibration using a plate target, a ball-and-socket scan mechanism, a spherical spiral path scan mechanism, and a wireless disposable laryngoscope.

16 Claims, 51 Drawing Sheets

(56) References Cited

U.S. PATENT DOCUMENTS

| | | |
|---|---|---|
| 6,306,092 B1 | 10/2001 | Yamrom et al. |
| 6,543,272 B1 | 4/2003 | Vitek |
| 6,604,404 B2 | 8/2003 | Paltieli et al. |
| 6,879,240 B2 | 4/2005 | Kruse |
| 7,110,583 B2 | 9/2006 | Yamauchi |
| 7,867,167 B2 | 1/2011 | Boctor et al. |
| 8,213,693 B1 | 7/2012 | Li |
| 8,216,146 B2 | 7/2012 | Hwang et al. |
| 8,357,093 B2 | 1/2013 | Willsie |
| 8,469,893 B2 | 6/2013 | Chiang et al. |
| 8,473,239 B2 | 6/2013 | Specht et al. |
| 8,540,583 B2 | 9/2013 | Leech |
| 8,672,851 B1 | 3/2014 | Quirk et al. |
| 2003/0236461 A1* | 12/2003 | Poland ............... G01N 29/0609 600/443 |
| 2005/0131302 A1 | 6/2005 | Poland |
| 2011/0230766 A1 | 9/2011 | Medlin |
| 2012/0053467 A1 | 3/2012 | Betts |
| 2012/0130246 A1* | 5/2012 | Haider ................. A61B 8/4477 600/447 |
| 2012/0238875 A1 | 9/2012 | Savitsky et al. |
| 2013/0055788 A1 | 3/2013 | Amit |
| 2013/0135288 A1 | 5/2013 | King et al. |
| 2013/0180312 A1 | 7/2013 | Jones |
| 2014/0046186 A1 | 2/2014 | Mauldin, Jr. et al. |
| 2014/0051984 A1 | 2/2014 | Berger et al. |

OTHER PUBLICATIONS

Verathon Inc., ScanPoint with QuickPrint User's Manual, 2008, 102 pages, Bothell, WA.

* cited by examiner

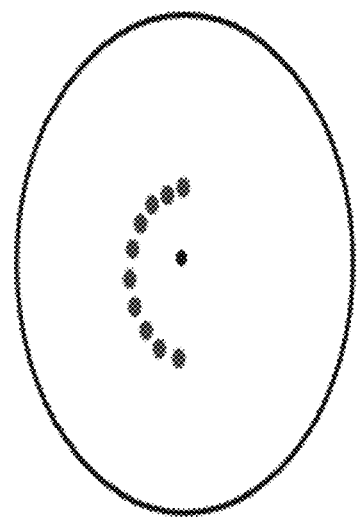
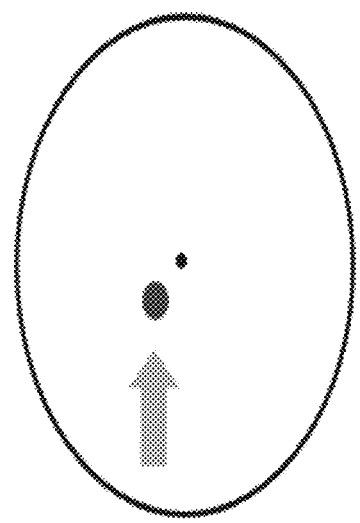
FIG. 7

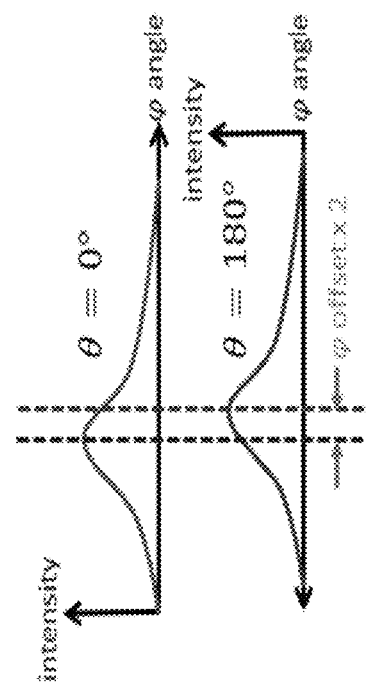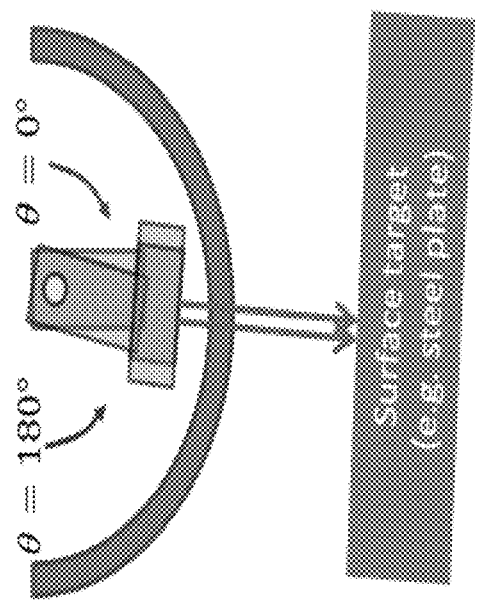
FIG. 25

ULTRASONIC DATA COLLECTION

CROSS-REFERENCE TO RELATED APPLICATION

This application claims priority to U.S. Prov. Appl. No. 61/936,232 filed Feb. 5, 2014, which is hereby incorporated by reference in its entirety.

BRIEF DESCRIPTION OF THE DRAWINGS

FIGS. 1-51 illustrate features according to one or more embodiments of the invention.

DETAILED DESCRIPTION OF THE PREFERRED EMBODIMENT

Figure 1:
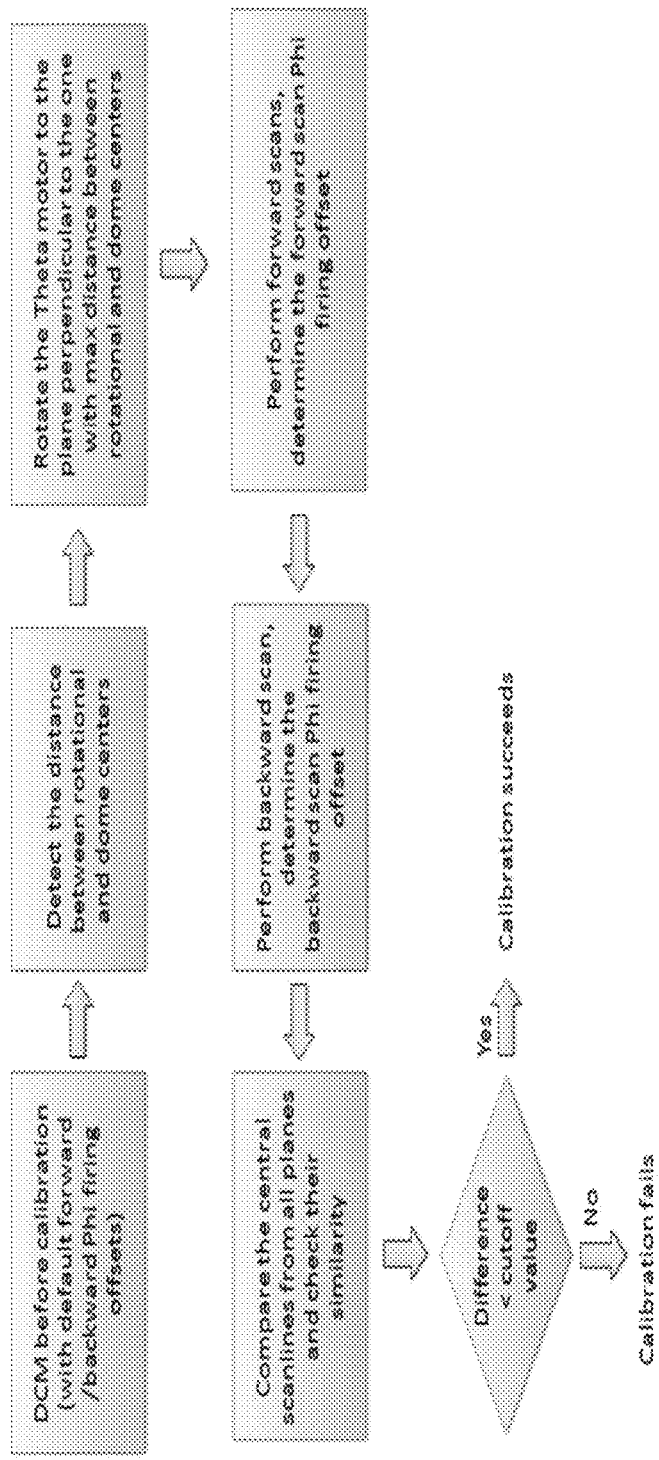

This patent application is intended to describe one or more embodiments of the present invention. It is to be understood that the use of absolute terms, such as "must," "will," and the like, as well as specific quantities, is to be construed as being applicable to one or more of such embodiments, but not necessarily to all such embodiments. As such, embodiments of the invention may omit, or include a modification of, one or more features or functionalities described in the context of such absolute terms.

Embodiments of the invention may be operational with numerous general purpose or special purpose computing system environments or configurations. Examples of well-known computing systems, environments, and/or configurations that may be suitable for use with the invention include, but are not limited to, electronic medical devices, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

Embodiments of the invention may be described in the general context of computer-executable instructions, such as program modules, being executed by a computer and/or by computer-readable media on which such instructions or modules can be stored. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Embodiments of the invention may include or be implemented in a variety of computer readable media. Computer readable media can be any available media that can be accessed by a computer and includes both volatile and nonvolatile media, removable and non-removable media. By way of example, and not limitation, computer readable media may comprise computer storage media and communication media. Computer storage media include volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

According to one or more embodiments, the combination of software or computer-executable instructions with a computer-readable medium results in the creation of a machine or apparatus. Similarly, the execution of software or computer-executable instructions by a processing device results in the creation of a machine or apparatus, which may be distinguishable from the processing device, itself, according to an embodiment.

Correspondingly, it is to be understood that a computer-readable medium is transformed by storing software or computer-executable instructions thereon. Likewise, a processing device is transformed in the course of executing software or computer-executable instructions. Additionally, it is to be understood that a first set of data input to a processing device during, or otherwise in association with, the execution of software or computer-executable instructions by the processing device is transformed into a second set of data as a consequence of such execution. This second data set may subsequently be stored, displayed, or otherwise communicated. Such transformation, alluded to in each of the above examples, may be a consequence of, or otherwise involve, the physical alteration of portions of a computer-readable medium. Such transformation, alluded to in each of the above examples, may also be a consequence of, or otherwise involve, the physical alteration of, for example, the states of registers and/or counters associated with a processing device during execution of software or computer-executable instructions by the processing device.

As used herein, a process that is performed "automatically" may mean that the process is performed as a result of machine-executed instructions and does not, other than the establishment of user preferences, require manual effort.

This invention disclosure discusses some potential optional advantage over the existing calibration method for certain types of ultrasonic scanner (which, in this document, may be referred to as the BladderScan product. An embodiment tries to solve three problems involved in the calibration process. First, the method detects the amount of misalignment between the transducer rotational and dome centers, which has been known to degrade the calibration results, and minimizes its negative impact on the calibration procedures. Second, the method tried to minimize the misalignment between image frames acquired by two-way scans caused by the gear backlash and/or machining errors. Third problem an embodiment tries to tackle is to enable the calibration without the use of water tank and external ultrasound target.

An embodiment proposes optional advantages over the existing calibration method for such ultrasonic scanners.

BladderScan product measures bladder volume by acquiring and analyzing three-dimensional (3D) cone-like ultrasound data. One of the most important factors in influencing the accuracy of volume measurement results with BladderScan is the geometrical structure, which is determined by a set of calibration parameters, of the acquired 3D ultrasound data. It was found that the calculation of calibration parameters with the existing algorithm is sensitive to the amount of misalignment between the transducer rotational and dome centers caused by the assembly errors. Thus, the first problem that the proposed method proposes to solve is to detect the amount of misalignment between the rotational and dome centers and minimize its negative impact on the calibration process.

Different from the BladderScan 9400, where only one-directional scan is taken, the next-generation BladderScan product performs two-way scan, where a data frame can be acquired by either moving the motor in a clockwise or anticlockwise direction or in both directions in succession. One of the advantages of two-way scan is that the frame rate of real-time B-mode is doubled compared to one-way scan given that the motor speed is the same for both cases. Also, the data acquisition time for 3D volume can be reduced by half. On the other hand, due to the potential machining errors and gear backlash, the data frames acquired by 2 different scans would not be automatically aligned with each other, leading to the misalignment of real-time B-mode imaging and the negative impact on the volume measurement accuracy. So the second problem an embodiment intends to solve is to align the ultrasound images acquired by two-way scans.

For the current BladderScan 9400 calibration process, a spiral-liked ultrasound target installed in a plastic water tank is used. An operator needs to fill the tank with enough amount of water in performing the calibration and empty the tank after the completion, which is time-consuming. Also, as discussed above, one assumption of the current calibration algorithm is the perfect alignment between the rotational and dome centers. Since the ultrasound target is placed in a water tank, there is also a requirement that the dome center should be aligned with the center of the spiral-liked target. Similar to the misalignment between the transducer rotational and dome centers, the small misalignment between the centers of the dome and the ultrasound target would also cause the incorrect Phi offset value and sometimes fail the calibration. Thus, by removing the need of water tank from the calibration process, we can eliminate one error source contributing to the inaccurate calibration results. So the third problem we want to solve is to enable the calibration without the use of any external fixtures, e.g., water tank and ultrasound target.

Three different approaches have been explored. The first approach (i.e., Algorithm I) deterministically calculates the amount of misalignment between the rotational and dome centers, estimates the Phi firing offset values for two-way scan, and detects the potential failure of a DCM. The second approach (i.e., Algorithm II) tries to solve the calibration parameters in a recursive optimization manner, where the optimal parameters are estimated by minimizing the difference between a sphere constructed by the calculated dome geometries and a perfect sphere. The third approach utilizes the cross-correlation in estimating the Phi offset and gear backlash values.

Algorithm I
Overview

Figure 2:
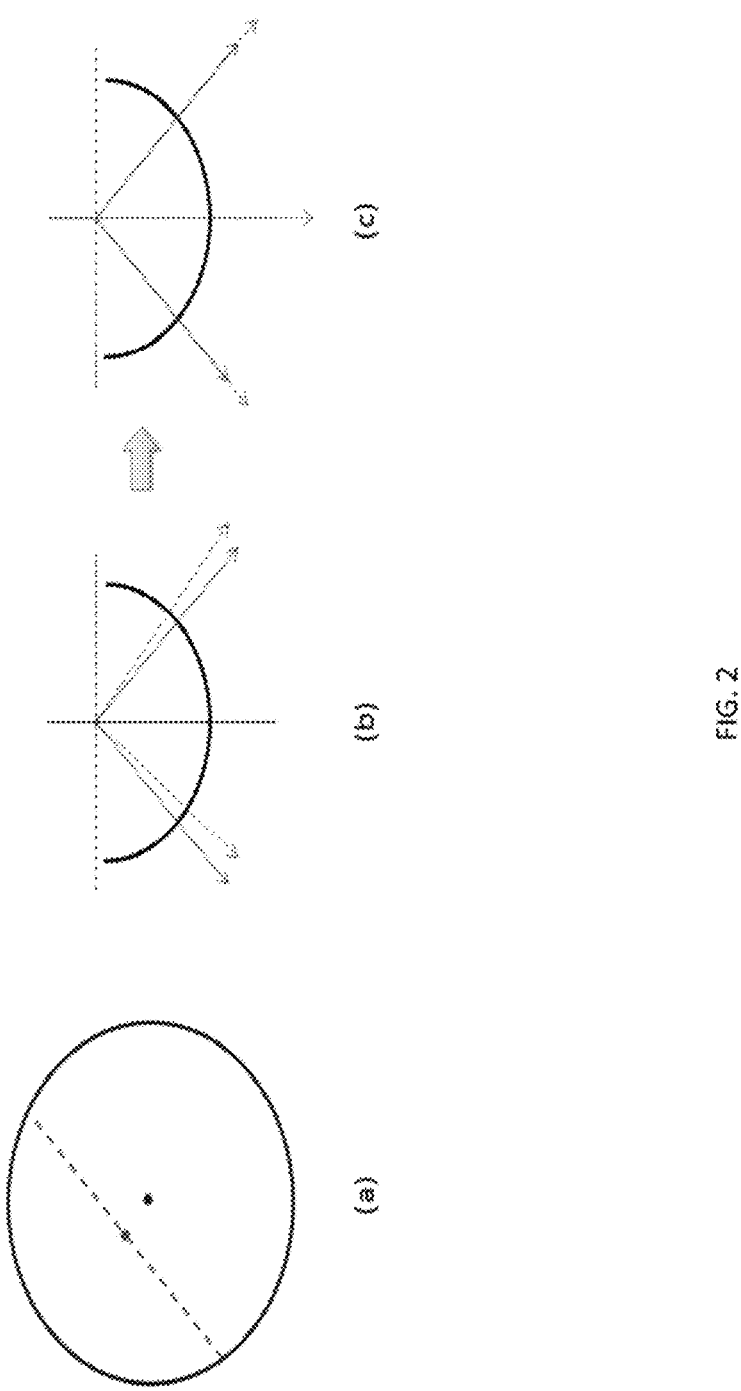

FIG. 1 shows the high-level block diagram of the proposed algorithm. The first step of the algorithm is to detect the distance between the rotational and dome centers (i.e., the amount of misalignment) of a BladderScan's data collection module (DCM). After detecting the misalignment as well as the corresponding plane with the maximum amount of misalignment, the algorithm rotates the Theta motor to the plane perpendicular to that plane. This process is more clearly illustrated in FIG. 2(a), where the blue circle represents the dome (viewing from the top of the probe). Instead of always performing the calibration in the first Theta plane, where the in-plane misalignment between the rotational and dome centers is potentially present, the proposed algorithm performs the calibration on the plane with the least amount of in-plane misalignment (FIG. 2(b)) so that the negative influence of the misalignment would be minimized. After the rotation of Theta motor, the algorithm determines the Phi firing offsets for forward and backward scans based on the symmetricity information of a data plane. With the calculated Phi firing offsets, the calibration algorithm commands the DCM to acquire a new set of 3D data, which is used for the detection of potential skewed spine of the DCM. Finally, the central scanlines from all data planes are compared in checking the similarity between them. If the difference between those scanlines is below a pre-defined cutoff value, then the calibration process succeeds. Otherwise, the calibration fails due to the severe skewness of the spine.

Step 1. Detection of Misalignment

Figure 3:
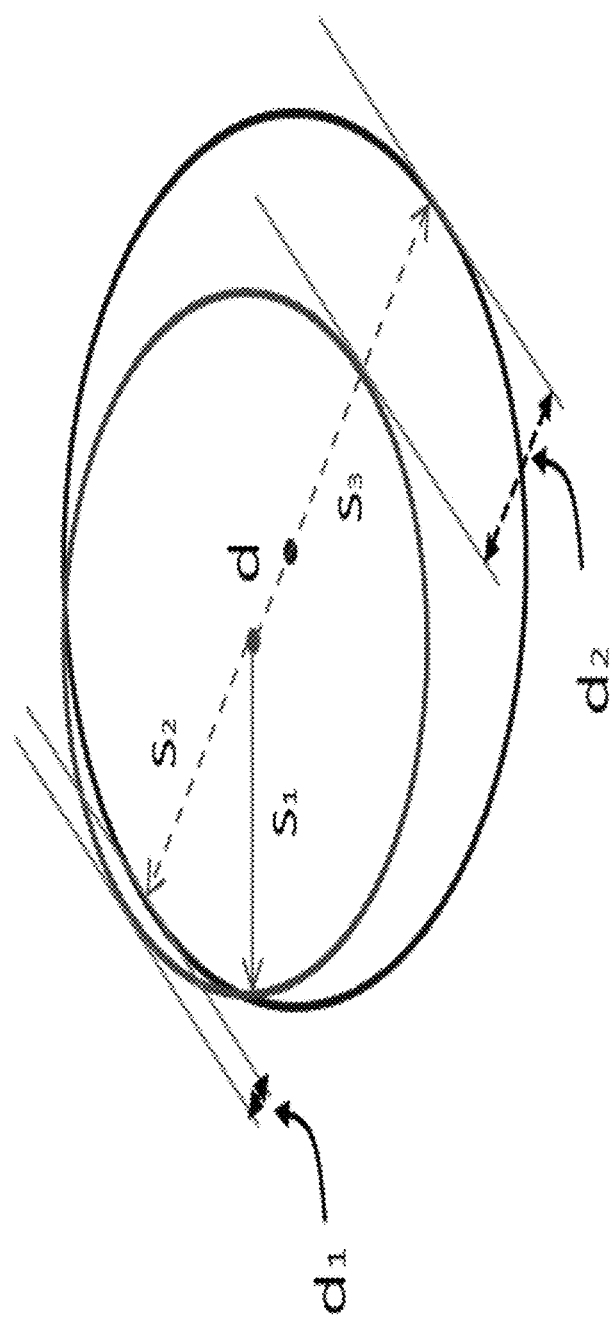

FIG. 3 gives the illustration of the misalignment detection algorithm. The blue circle represents the dome (viewing from the top of the probe) and the blue dot is the dome center. The red dot represents the rotational center and the red solid line stands for the first scanline in the first Theta plane. The length of the red solid line represents the distance between the rotational center and the wall of the dome. The red circle was formed by rotating the red solid line 360 degree around the rotational center (i.e., red dot).

Assuming that there is no misalignment between the rotational and dome centers, i.e., the red and blue dots are at the same location, then the red and blue circles should also be overlapped with each other. It means that the distance from the rotational center (i.e., red solid line) should be the same for all Theta planes. However, due to the misalignment between the rotational and dome centers, the red and blue circles would be no longer overlapped with each other as shown in FIG. 3. The distance between the rotational center and the dome would be varied for different planes. In FIG. 3, the shortest and longest distance between the rotational centers and the dome is denoted as S2 and S3, respectively.

Theoretically, the distances S1, S2 and S3 can be estimated based on the reverberation patterns present in the reflected ultrasound echo as discussed in Algorithm II. However, the calculation is relatively sensitive to noise. Based on the relative displacement between the lines S1, S2 and S3, the distance between the rotational (red dot) and dome (blue dot) centers can be estimated via the following equations:

$$d_1 = \mathrm{disp}(S_2, S_1) \tag{1}$$

$$d_2 = \mathrm{disp}(S_3, S_1) \tag{2}$$

$$d = (\mathrm{abs}(d_1) + \mathrm{abs}(d_2))/2 \tag{3}$$

where disp(,) calculates the displacement between 2 signal and converts it to the distance, abs( ) obtains the absolute value, d1 and d2 represent the distance difference between S1 and S2 and between S1 and S3, respectively, and d is the amount of misalignment between the rotational and dome centers.

After obtaining the amount of misalignment between the rotational and dome centers, we also know which of plane has the maximum amount of in-plane misalignment. So the algorithm can command the DCM to rotate the Theta motor to the plane perpendicular to the one with maximum in-plane misalignment (FIG. 2(a)) and perform the rest of the calibration procedures.

Figure 4:
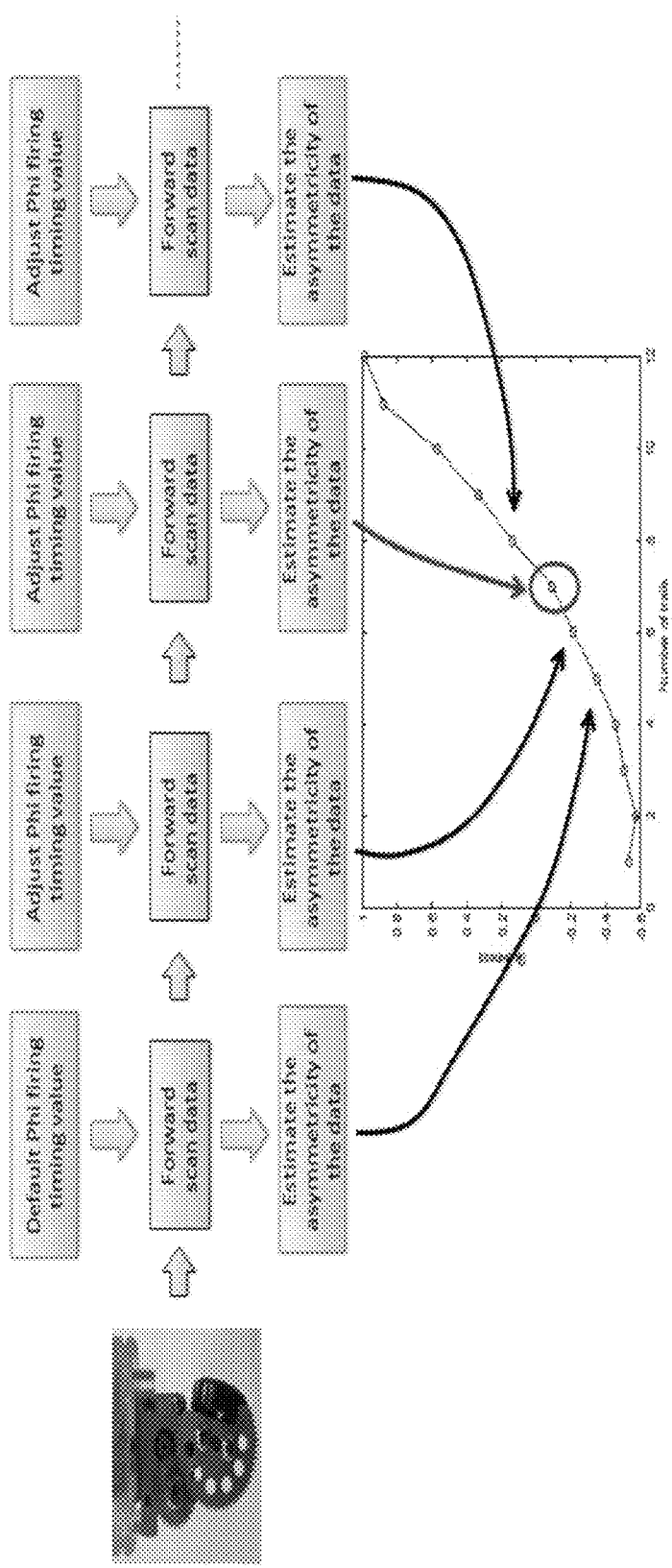

Step 2. Determination of Forward Scan Phi Firing Offset, which is the Blind Spot from Home (Vertical) to the Angle at Which Data Begins to be Collected by the Transducer The purpose of the forward scan Phi firing offset value is to determine the first scanline (i.e., first ultrasound transmit) position during the forward scan in ensuring that the forward scan frame is symmetrical. The forward scan Phi firing offset value can be iteratively determined based on the symmetricity information of data frame as shown in FIG. 4. Starting with a default Phi firing offset value, a forward scan data is acquired and the asymmetricity of the data is estimated. Based on the amount of asymmetricity, the Phi firing offset value is adjusted and updated, after which a forward scan data is acquired again with the updated Phi firing offset value. This procedure is repeated multiple times as shown in FIG. 4 until the blue dot curve crosses the zero value, suggesting that the optimal Phi firing offset value is found as the amount of data asymmetricity is minimal. And this forward scan Phi firing offset value can be saved as one of the scan parameters and also used for the rest of calibration process.

Step 3. Determination of Backward Scan Phi Firing Offset

After ensuring that the forward scan frame is symmetrical, the algorithm tries to match the backward scan to the forward scan frame. The reason why the Phi firing offset for the backward scan frame is not determined through the same steps as shown in FIG. 4 is that there is potential gear backlash that would make the forward and backward scan frames misaligned with each other. To compensate the gear backlash, different approach is used in determining the backward scan Phi firing offset value.

Figure 5:
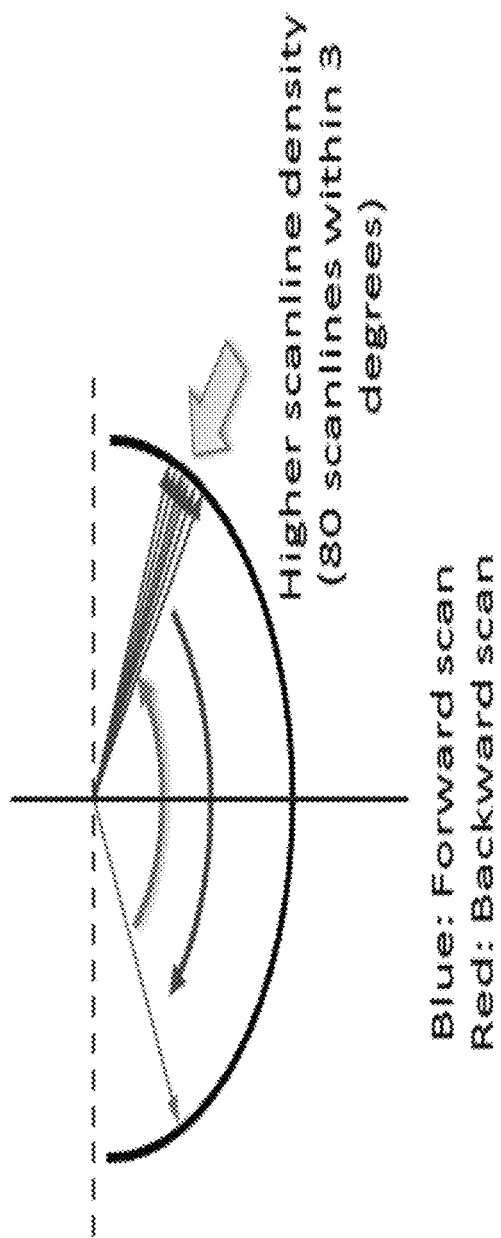

The procedures that determine the Phi firing offset value for backward scan is shown in FIG. 5. The blue color lines represent the scanlines from the forward scan and the red color lines the scanlines of the backward scan. In order to align the forward and backward scans, we need to align the last scanline of the forward scan (blue) with the first scanline of the backward scan (red). As the space interval between 2 consecutive scanlines is reasonably the same as the motor runs in a constant speed, so the alignment between the forward and backward scan planes would be achieved by aligning the last scanline of the forward and the first scanline of the backward scans.

To minimize the time in searching the best match between the 2 scanlines from the forward and backward scans, a much higher density of scanlines are formed by transmitting and receiving the ultrasound signal more frequently as shown in FIG. 5. The ultrasound signature of each scanline would be varied between each other as the ultrasound signal is reflected back from different regions of dome while the motor moves. When 2 scanlines are reflected from the same spot of the dome, the correlation between them should be maximized. By computing the correlation between the last scanline of the forward scan and every scanlines (high density) collected during the backward scan, the best-matched scanline from the backward scan can be identified and the timing of the scanline can be used for the Phi firing offset value for the backward scan.

Step 4. Detection of Skewed Spine

Figure 6:

One of the major sources contributing to the inaccurate bladder volume measurement is the skewed spine shown in FIG. 6(b), where TXU stands for the transducer that moves in and out of the paper. It is optionally advantageous to detect the potential skewed spine in a DCM and preferably compensate the volume measurement inaccuracy.

After determining the Phi firing offset value for the forward and backward scans, assuming that the spine of a DCM is not considerably skewed, the central scanlines from all image planes should be largely similar as they are reflected from the reasonably same spot of the dome as shown in FIG. 7(a). On the other hand, due to the skewed spine in FIG. 7(b), the central scanlines from different planes would intersect with the dome at different locations, where a larger skewed spine would lead to a bigger difference between central scanlines. When the amount of difference between scanlines (measured by the correlation coefficient) exceeds a pre-defined cut-off value, which can be determined by correlating it with the volume inaccuracy, the calibration algorithm should notify customers about the failure of a DCM as shown in FIG. 1.

Algorithm II

Figure 8:
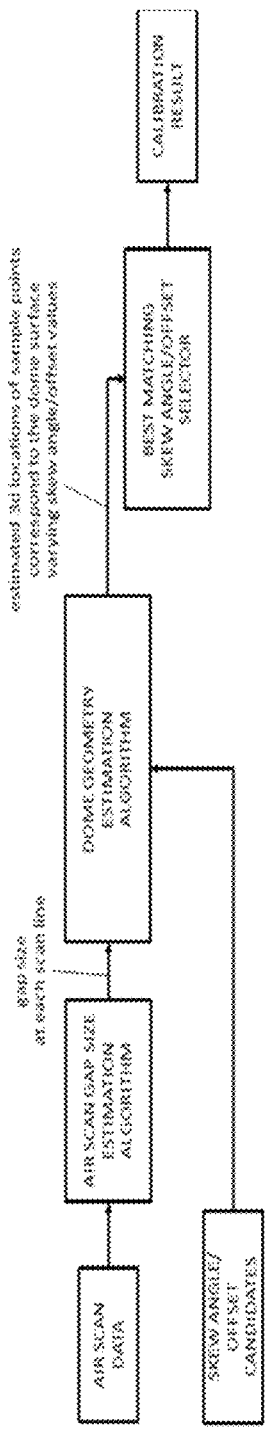
Figure 9:
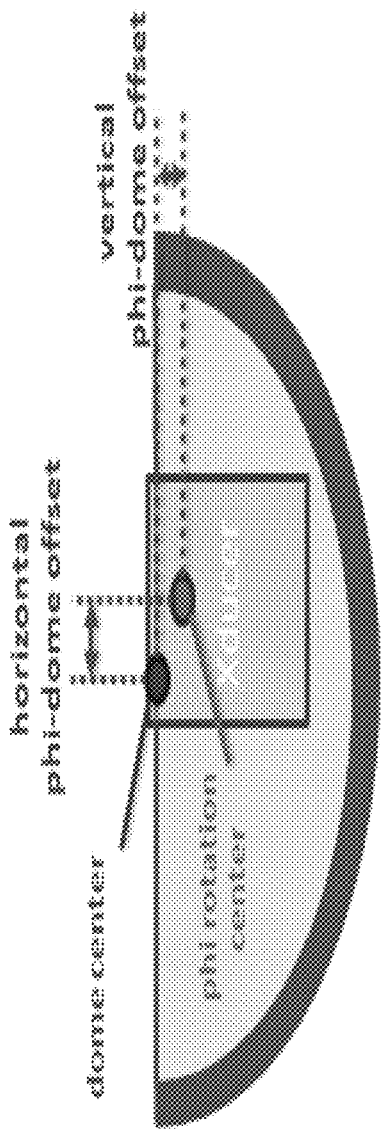

For this algorithm, we use the principal that the gap size between the consecutive patterns is determined as the distance between the transducer and the dome surfaces. By combining the gap size information with the transducer position information obtained from the Phi/Theta tables and skew angle/offset values, the location of a sample point that corresponds to the dome surface at each scan line, i.e., dome geometry, can be estimated. This process can be repeated using various skew angle/offset values until we obtain dome geometry that is closest to a perfect sphere. The skew angle/offset value information that corresponds to the best matching dome geometry is used as calibration parameters. As this algorithm relies on the distance between the transducer and the dome surface, intentional offset value between the transducer rotation and dome center is desirable to avoid undetectable motion errors due to the symmetry (FIG. 9). For example, if transducer rotation and dome center is the same, erroneous offset value in transducer Phi motion cannot be detected because transducer-dome distance is constant regardless of Phi offset. Number of planes and scan lines acquired could vary depending on the system. Followings are the detailed procedures for the proposed calibration algorithm (FIG. 8).

Step 1. Collect Ultrasound Data

As the first step of the calibration, ultrasound data is collected in the air (i.e., without water tank and ultrasound target).

Step 2. Estimate Gap Size Between Air Scan Patterns

Figure 10:
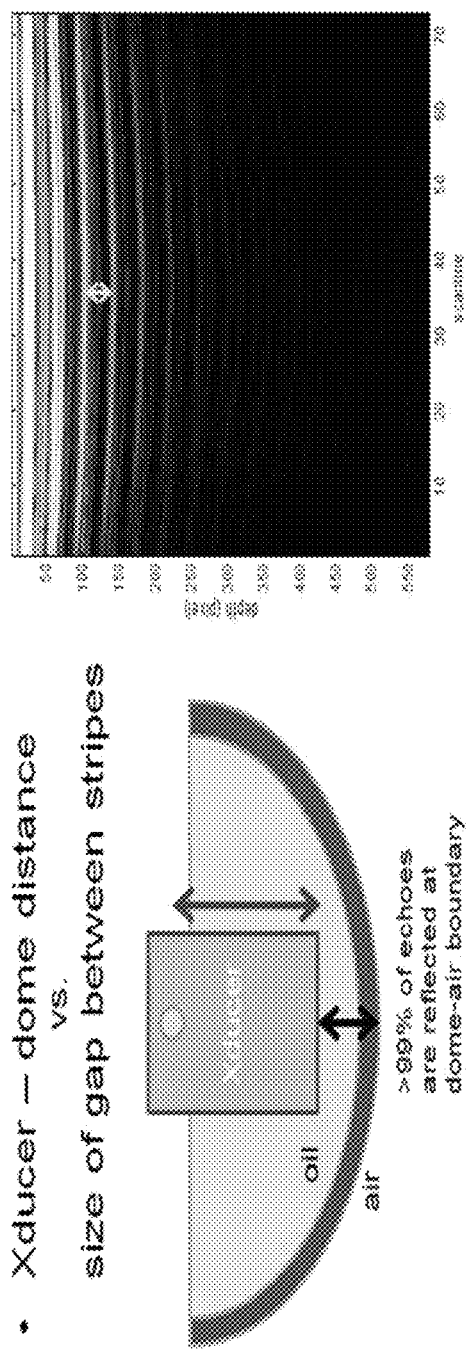
Figure 11:
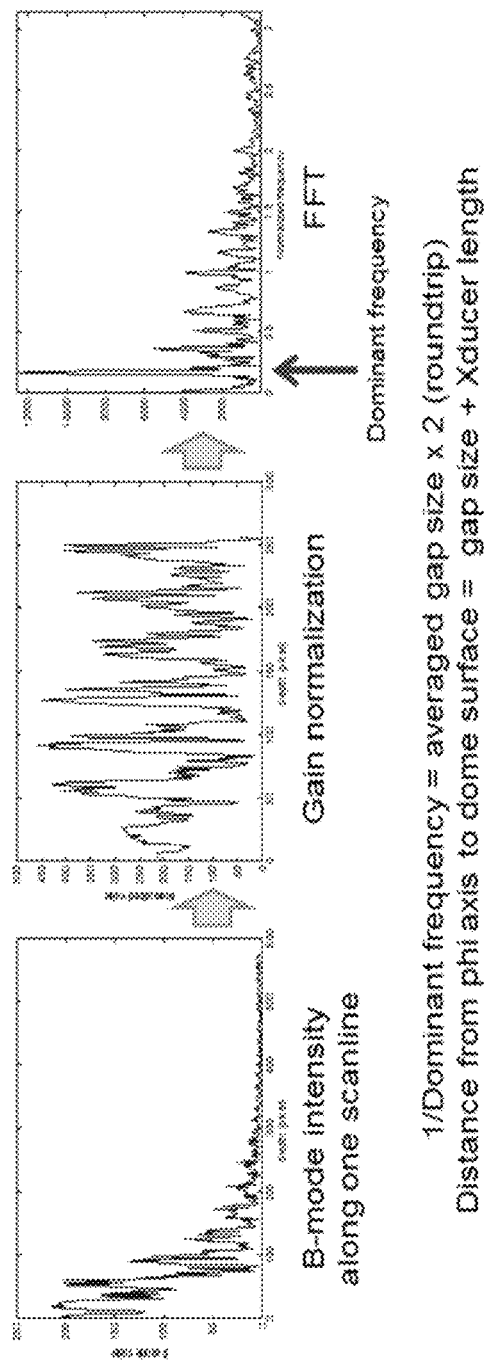

Gap size between the consecutive air scan reverberation patterns is proportional to the transducer-dome distance (FIG. 10). Gap size can be detected in B-mode image by detecting air scan pattern. As a more advance method, dominant spatial frequency of the reverberation pattern can be detected to estimate gap size more accurately (FIG. 11).

Step 3. Estimate Dome Geometry

Figure 12:
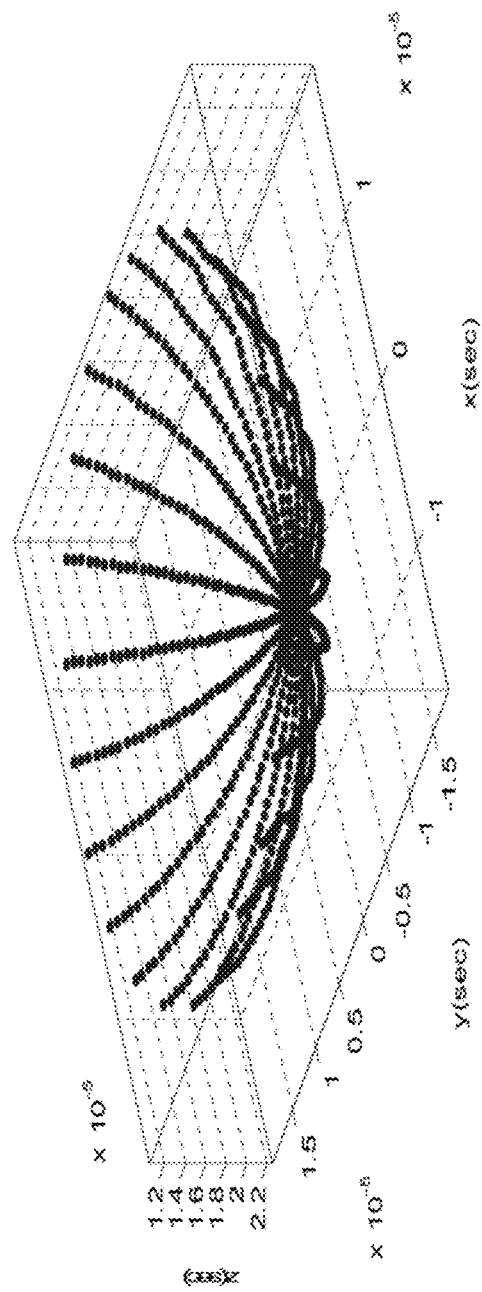

If we assume that there is no error in transducer motion, 3D location of the transducer for each scan line can be derived from the Phi and the rotation information. Then, the location of a sample point that corresponds to the dome surface in each scanline can be estimated by using the gap size information at the scanline. An example of this dome geometry estimation results is shown in FIG. 12. In the same way, dome geometry can be estimated when transducer motion error exists. This dome geometry estimation process is repeated many times by varying transducer skew angles and offset values.

Step 4. Select the Best Matching Skew Angle/Offset Values

Figure 13:
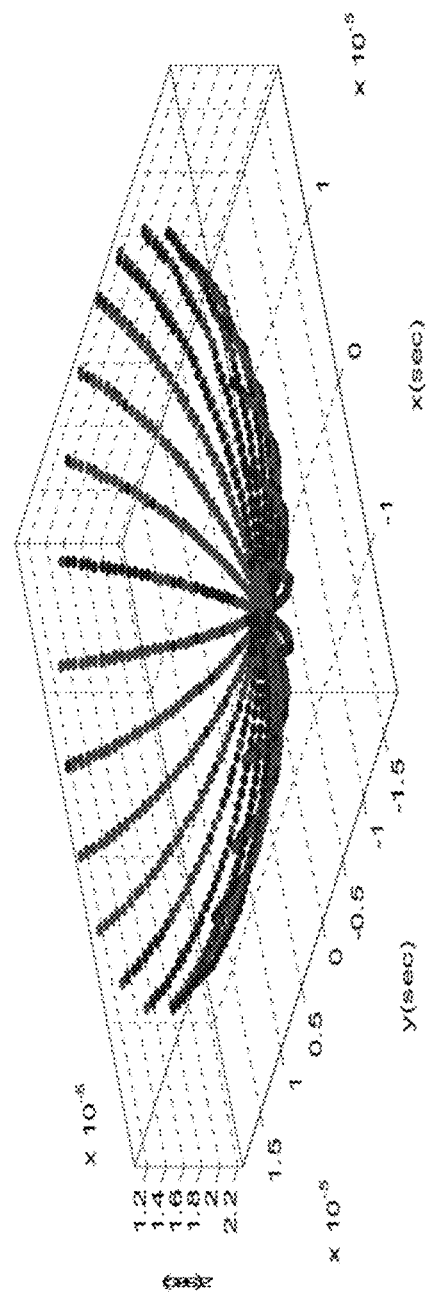

A best fitting sphere can be determined for each of the estimated dome geometries (FIG. 13). Based on the assumption that dome shape is perfectly spherical, the dome geometry that resulted in the smallest deviation (e.g., mean squared error) from its fitting sphere is selected as the best matching case. The corresponding skew angle and offset values to the best matching case can be considered as the calibration result.

Algorithm III

Figure 14:
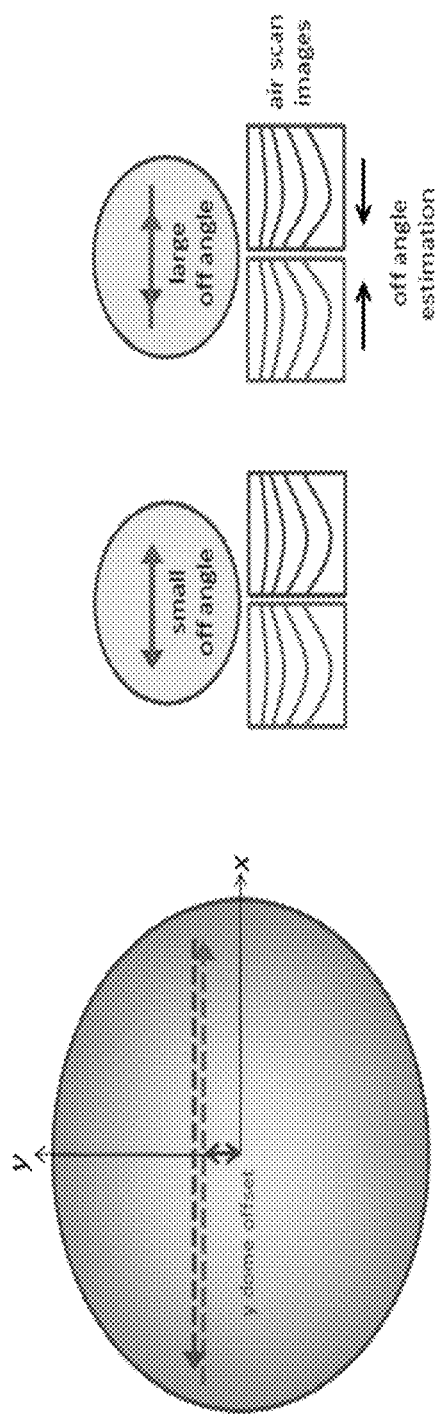

One of the main purposes of the calibration process is to estimate appropriate phi offset and firing delay values to make the orientation of the B-mode image correct. This can be done by comparing a B-mode image with another one at the same scan plane after 180° theta rotation as shown in FIG. 14. To increase the sensitivity of the off-angle detection, an intentional offset between phi rotation and dome center (FIG. 9) would be desirable.

Figure 15:
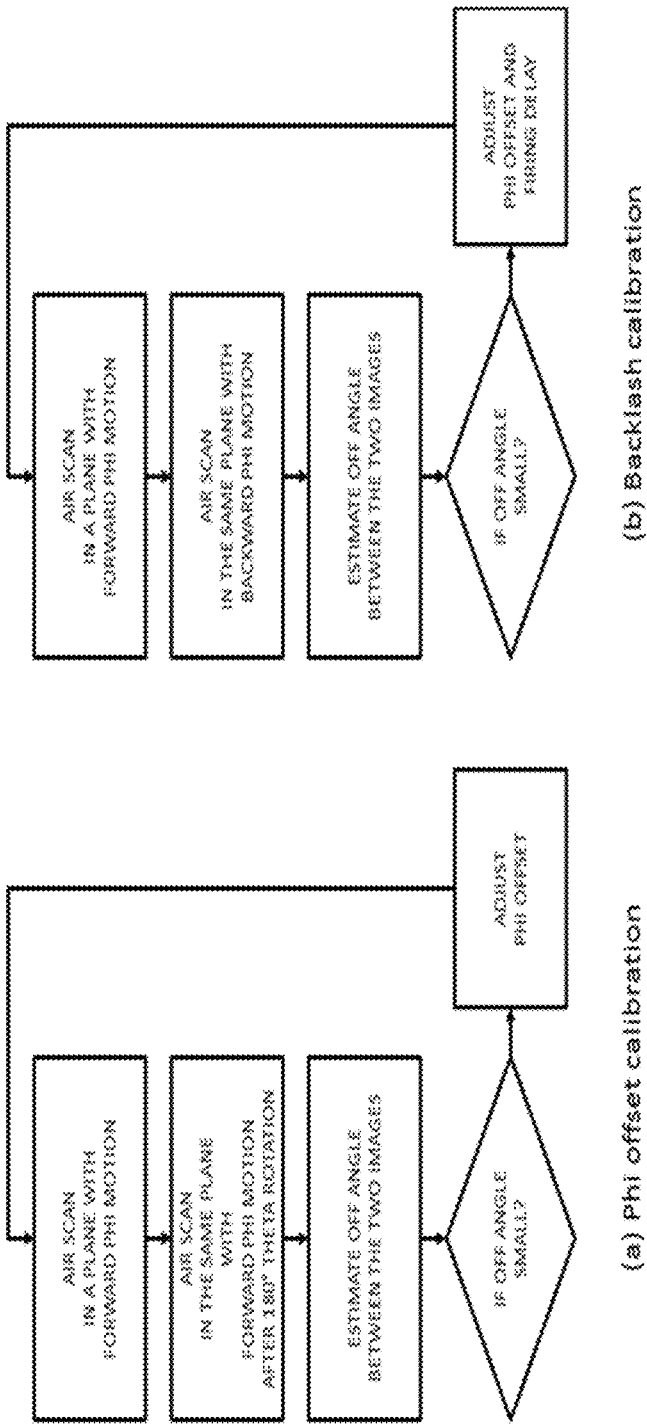
Figure 16:
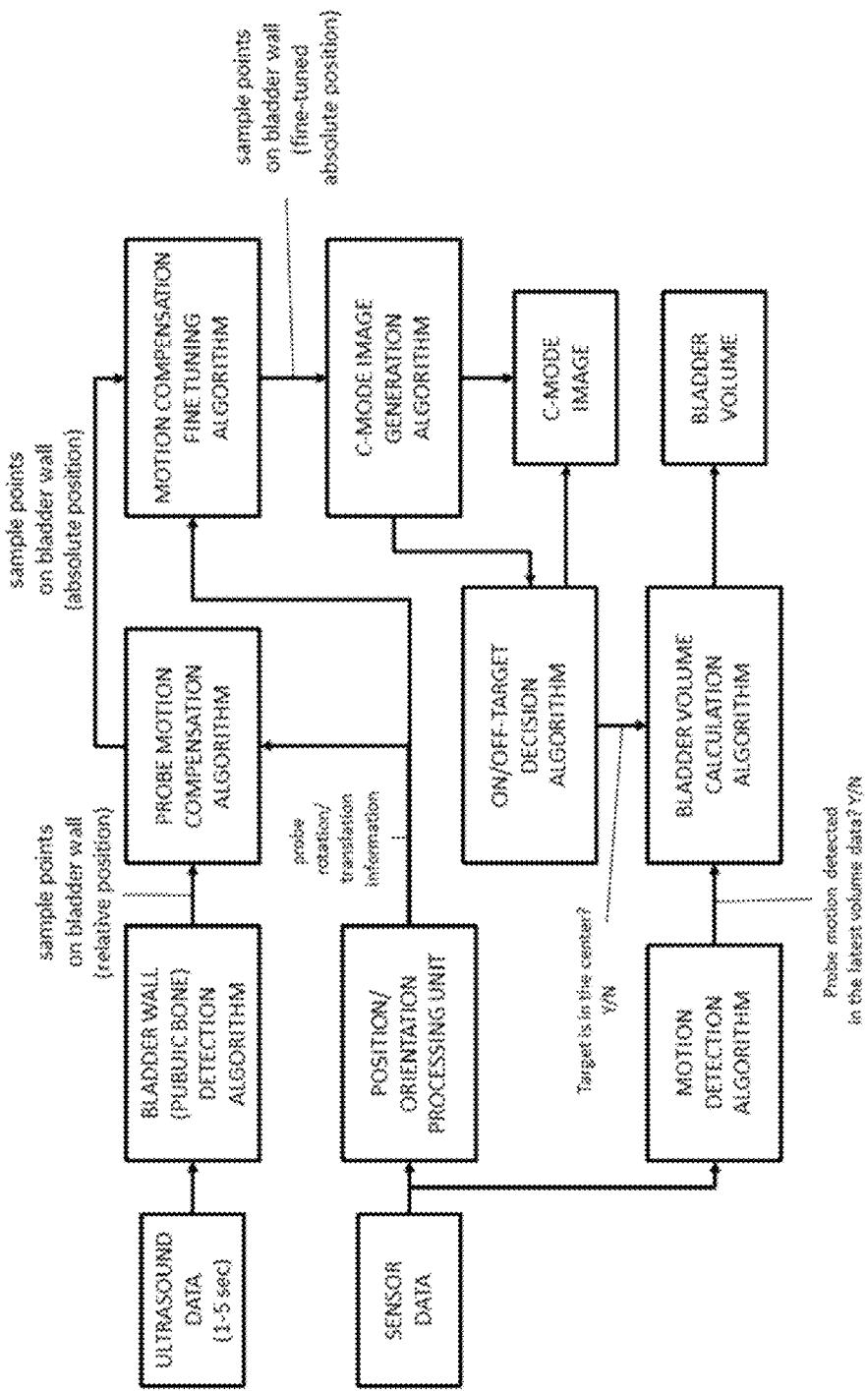

Some small errors in the phi motion itself, e.g., gear backlash, cannot be detected using the above procedure. To estimate the phi offset and firing delay values to compensate the gear backlash, an additional step is optionally advantageous. This process is basically the same with FIG. 14, except for comparing images acquired with different phi motions without moving the theta motor. The detailed step-by-step procedure for the simple air scan calibration is as follows (FIG. 15):

a. Phi Offset Calibration

Step 1: Collect air scan data (B-mode) in a scan plane.

Step 2: Collect another air scan data in the same plane with the same phi motion after 180° theta rotation.

Step 3: Estimate the phi angle difference between the two B-mode images. Cross correlation of the two images can be used as a simple estimation method.

Step 4: If the estimated phi angle difference is small enough, use the current phi offset/firing delay value for calibration. Otherwise, adjust the phi offset/firing delay according to the difference, then repeat steps 1-4.

b. Backlash Calibration

Step 1: Collect air scan data (B-mode) in a scan plane with forward phi motion.

Step 2: Collect another air scan data in the same plane with backward phi motion.

Step 3: Estimate the phi angle difference between the two B-mode images. Cross correlation of the two images can be used as a simple estimation method.

Step 4: If the estimated phi angle difference is small enough, use the current phi offset/firing delay value for backlash calibration. Otherwise, adjust the phi offset/firing delay according to the difference, then repeat steps 1-4.

Method for Real-Time C-Mode Using Position Sensor

Three-dimensional ultrasound has a limit in the achievable volume rate because of the delay times for sound wave travel and/or mechanical transducer motion. With the current ultrasound bladder scanners that have the same limitation, severe motion blur occurs if a probe does not stay still during scanning. For this reason, most bladder scanners do not provide real time imaging modality for probe aiming. Some recently introduced bladder scanners support real time B-mode by restricting the transducer motion within one plane for higher frame rates. This B-mode is useful, but still inconvenient because B-mode imaging plane is perpendicular to the plane of probe motion. Instead, as an ideal aiming guide, this invention introduces real-time C-mode bladder imaging and two methods to implement it. The first method uses probe translation/rotation information derived from position sensors to compensate for probe motion. The other method uses a new user interface to make the user interpret the motion-blurred data more efficiently.

Three-dimensional ultrasound has a limit in the achievable volume rate because of the delay times for sound wave travel. With mechanical 3D probes, the limitation becomes stricter due to the additional delay for transducer motion, which is the case of the current ultrasound bladder scanners that typically require 2-3 seconds for volume scanning With this low volume rate, probe motion by an operator could produce severe motion blur in the ultrasound data. On this account, the majority of the current ultrasound bladder scanners have not provided real time imaging modality. This caused inconvenience in aiming a probe. Recently, some new bladder scanners provide real time B-mode by restricting the transducer motion within one plane for higher frame rates, but the B-mode is still far from the ideal imaging modality for probe aiming because it provides only partial information on the bladder location and shape. In addition, B-mode is not easy to use because imaging plane is perpendicular to the plane of probe motion. In contrast, C-mode is very intuitive because its imaging plane is parallel to the probe motion. However, C-mode is difficult to implement in real time with low volume rate probes because it requires full 3D volume data.

An embodiment of the present invention introduces new methods for real time C-mode bladder imaging as ideal probe aiming guides. The first method uses sensors, e.g., inertial measurement unit, magnetic and optical sensors, etc., that can be used for measuring/deriving probe location and orientation information in combination with ultrasound data. Summarized real time C-mode process with a position sensor is as follows:

a. Acquire ultrasound and probe location sensor data synchronized with each other in real time.

b. Detect sample points that correspond to the bladder wall at each scan line from the ultrasound data acquired for the most recent 1-5 seconds.

c. Derive relative location information of the bladder wall sample points from the probe.

d. Derive absolute probe location and orientation information from the position sensor data at each scan line; derive the probe translation and rotation information at each scan line.

e. Convert the relative bladder wall sample locations to the absolute locations by compensating for the probe translation and rotation at each scan line.

f. Optimize the probe motion compensation based on the absolute bladder wall locations; fine tune the probe motion parameters to make the congregated sample points a bladder-like shape.

g. Calculate projections of the motion-compensated bladder wall sample points to the plane perpendicular to the sightline of the probe; estimate the bladder shape from the viewpoint of the probe. Generate C-mode image from the projection.

h. Check the location of the bladder center in the C-mode. If it has been well centered for a certain period of time, turn on the on-target indicator (or automatically start volume measurement).

i. (Optional) Detect probe motion in the latest volume data. If there is no large motion, calculate and display bladder volume instantaneously using the data in the buffer when requested for responsiveness.

The second method does not use position sensor, but uses a new user interface (UI) utilizing the fact that human eye can perceive accurate object position by estimating its motion if the blurred object looks like a comet with tail. This new UI can be implemented by making the bladder walls that correspond to the more recent data have a deeper color or lower transparency. Although this new C-mode still has motion blurs, it would provide all the information necessary for probe aiming. Summarized real time C-mode process with the new UI is as follows:

a. Acquire ultrasound and probe location sensor data synchronized with each other in real time.

b. Detect sample points that correspond to the bladder wall at each scan line from the ultrasound data acquired for the most recent 1-5 seconds.

c. Derive relative location information of the bladder wall sample points from the probe.

d. Generate C-mode images from the bladder wall information. Make the more recent information less transparent or have deeper color to make the motion-blurred C-mode look like a comet with tail.

e. Check the location of the bladder center in the C-mode. If it has been well centered for a certain period of time, turn on the on-target indicator (or automatically start volume measurement).

a. Difficult probe aiming with ultrasound bladder scanners: No ultrasound bladder volume scanner has ever provided a real time C-mode that shows bladder shapes from the viewpoint of the probe head. Different from the B-mode that requires training to be accustomed to, C-mode is very intuitive because image plane is parallel with the plane of probe motion, which is similar to seeing a bladder through a virtual window on the skin surface.

b. Probe motion during bladder volume measurement (position sensor method): Start button on the probe causes small probe motion that could increase inaccuracy in bladder volume measurement. In real time C-mode, the device can automatically start volume measurement when the bladder is right on the target without any button push by an operator. In addition, accelerometer monitors probe motion during the volume data acquisition. If large motion is detected, the device can flash a warning sign or automatically repeat data collection until the probe stands still.

c. Probe-console alignment problem (position sensor method, optional): By tracking the absolute orientation of the probe, orientation of the C-mode display can be automatically aligned with the probe orientation. Thus, operator can perform examination from both sides of the patient regardless of the console location without any confusion or manual display adjustment.

Figure 17:
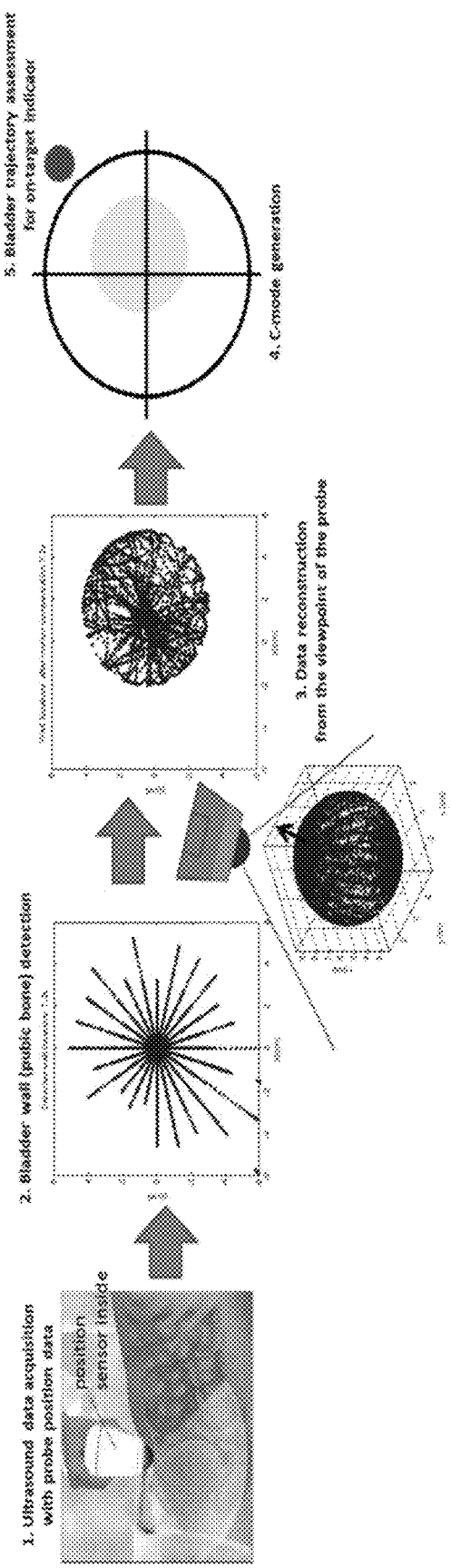

Method 1: Real-Time C-Mode using Position Sensor
Detailed Real-Time C-Mode Process with Position Sensor:
Step 1: Data Acquisition Ultrasound and probe position/rotation sensor data synchronized with each other in real time are acquired (FIG. 17.1). Inertial measurement unit (IMU) that consists of three-axis accelerometers, magnetometer sand gyroscopes is an example of the position sensor. An optical sensor with markers, a magnetic sensor with a transmitter, or any combinations of IMU, optical and magnetic sensors can be used for position tracking Data buffer should be large enough to store data acquired for the most recent 1-5 seconds.

Step 2: Bladder Wall Detection

Sample points that correspond to the bladder wall are detected at each scan line from the ultrasound data acquired for the most recent 1-5 seconds. BVI9400 algorithm or any new algorithm can be used for this process. From the detection results, relative 3D location information of bladder wall sample points is derived. At this stage, bladder wall location is relative from the probe at each scan line, i.e., probe motion is not compensated and may have motion blur (FIG. 17.2).

Step 3: Probe Location/Orientation Estimation

From the position sensor data, probe location and orientation information is estimated at each scan line.

Step 4: Probe Motion Compensation

Relative bladder wall locations are converted into the absolute locations by compensating for the probe translation and rotation at each scan line (Fig. between 17.2 and 17.3).

Step 5: Fine Tuning of the Motion Compensation (Optional)

Output of the position/rotation sensor is not stable sometimes, especially with an IMU. For example, a small offset in accelerometer output could cause several inches of error in the estimate translation value. Thus, an additional step to stabilize the motion compensation result would be desired. One of the possible approaches is estimating the sensor offset values to make the resulting bladder wall sample points to form a sphere-like shape (or, alternatively, as close as possible each other). If there is another sensor that can measure the location of the probe, e.g., optical sensors, it can be used to compensate for the accelerometer/gyroscope errors.

Step 6: C-Mode Image Generation

To make a C-mode, or to estimate the bladder shape from the viewpoint of the probe, projections of the motion-compensated bladder wall sample points to the plane perpendicular to the sightline of the probe are calculated (FIG. 17.3). By detecting the outline of the projected sample points, C-mode image can be generated (FIG. 17.4). Scan lines that pass through the pubic bone can be also detected in this procedure using the 9x or similar algorithm.

Step 7: On-Target Indicator

From the generated C-mode, it can be determined whether the bladder is centered enough or not. If it is well centered for a certain period of time, e.g., 2 seconds, an on-target indicator can be turned on (FIG. 17.5). This on-target indicator can be also used for triggering bladder volume calculating process.

Step 8: Probe Motion Detection (Optional)

Optionally, accelerometer data can be used for detecting probe motion for the most recent 1-2 seconds. Based on this information, integrity of the most recent volume data can be checked, which means bladder volume calculation can be done using the data already in the data buffer. This enables a responsive bladder volume display.

Method 2: Real-Time C-Mode with an Improved User Interface

Figure 18:
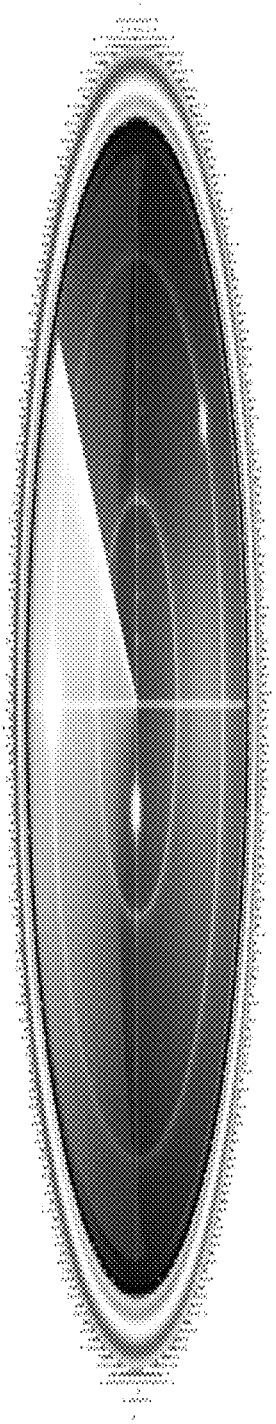

If position sensors are not used, motion blur in C-mode is unavoidable. Even in this case, however, a new user interface (UI) can make the blurred C-mode less annoying and more usable. For example, in a radar display that typically has a very low frame rate (FIG. 18); more recent data are displayed in a brighter color. So, user can track object positions more accurately by putting more weight on the brighter information.

Figure 19:
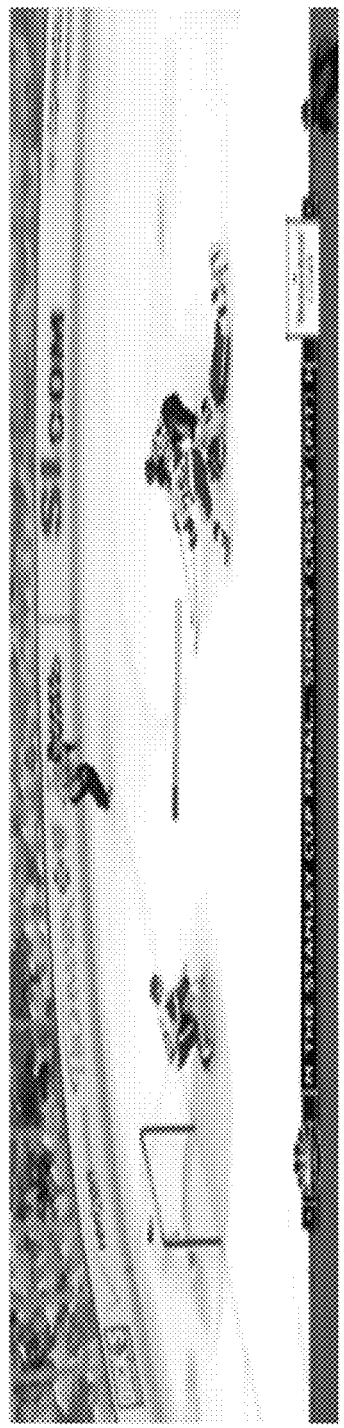
Figure 20:
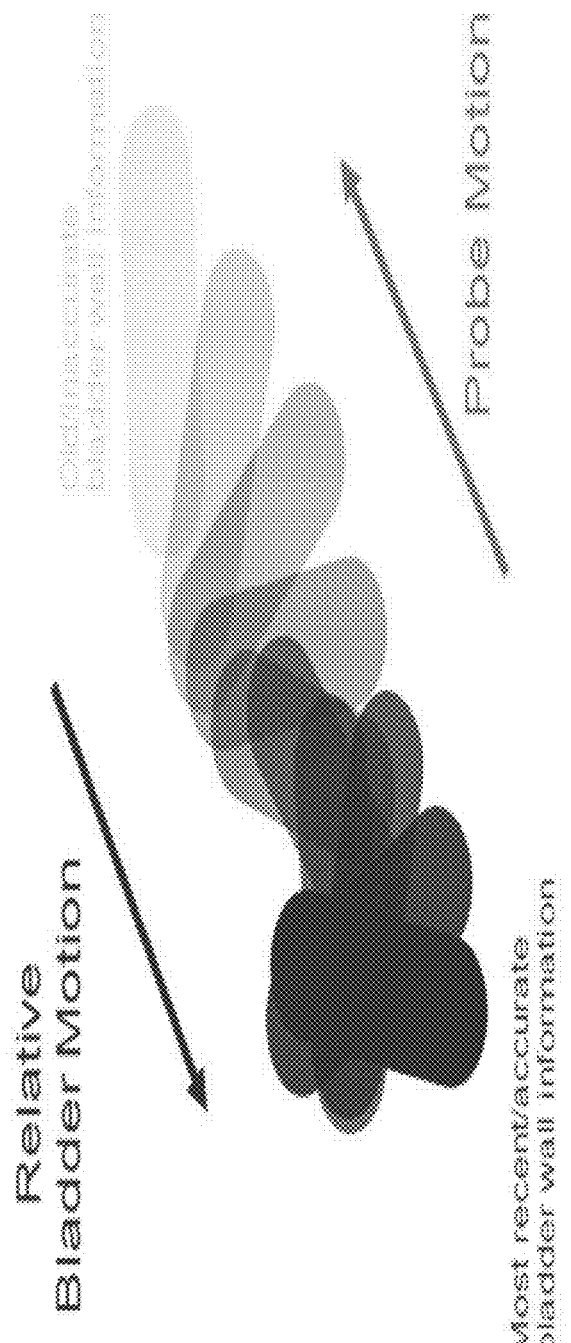
Figure 21:
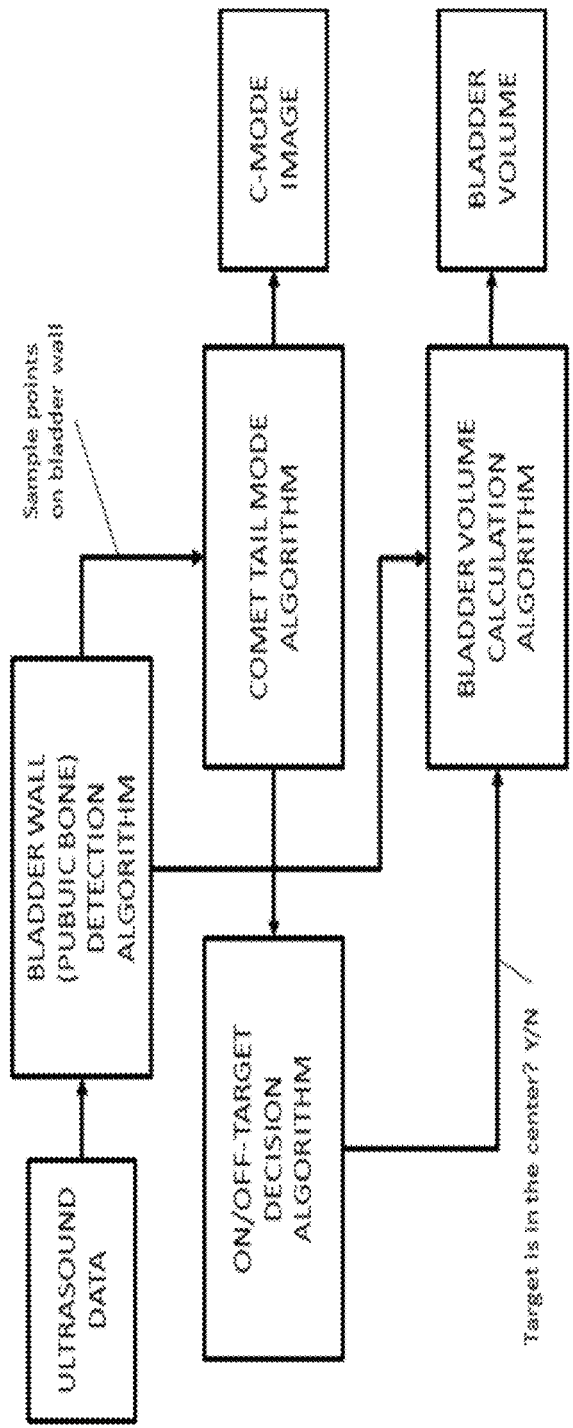

Another example is hockey puck enhancement technology that looks like a comet with a tail (FIG. 19). Although the comet tail is a kind of motion blur, it does not confuse the object position, but rather helps in estimating the next position of the puck. This is because human visual system naturally perceives the direction and speed of the motion from the comet tail-like object shape.

For real-time C-mode, a similar approach can be applied. The new UI is basically similar with the 9x C-mode, i.e., plotting the location of the detected bladder wall locations on the x-y plane. However, the new UI displays the more recent data less transparently (or in a darker color, etc.) to make the bladder trajectory like a comet with a tail. In this mode, human eye focuses on the "comet head" and naturally tracks its motion based on the shape of the comet tail (FIG.

20). Although this new C-mode looks different from the traditional C-mode, it provides all the necessary information for aiming in an intuitive way.

Detailed Real-Time C-Mode Process with a New UI:

Step 1: Data Acquisition

Figure 22:
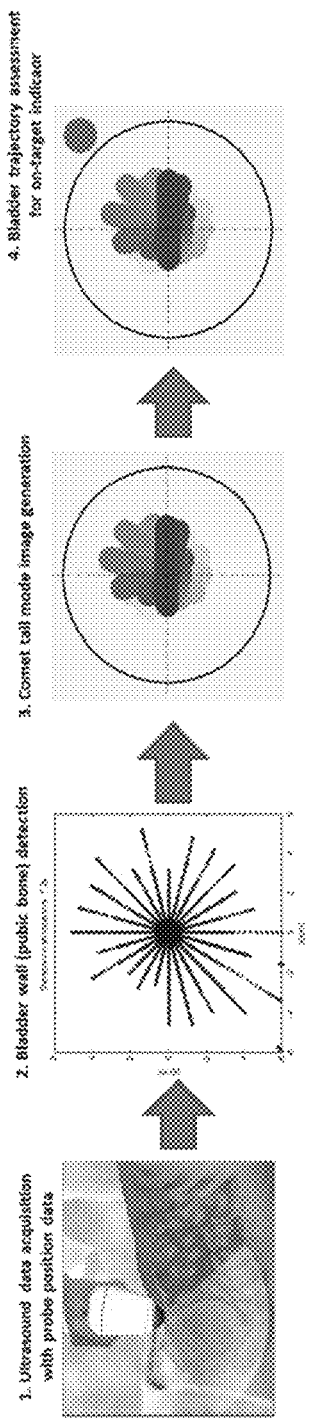

Ultrasound and probe position/rotation sensor data synchronized with each other in real time are acquired (FIG. 22.1). Data buffer should be large enough to store data acquired for the most recent 1-5 seconds.

Step 2: Bladder Wall Detection

Sample points that correspond to the bladder wall are detected at each scan line from the ultrasound data acquired for the most recent 1-5 seconds. BVI9400 algorithm or any new algorithm can be used for this process. Through this process, all the scan lines are classified into two groups; 1) scan lines that pass through the bladder and 2) the others (FIG. 22.2). Scan lines that pass through the pubic bone can be also detected in this procedure using the 9x or similar algorithm.

Step 3: C-Mode Image Generation

In the comet tail mode, scan lines that pass through the bladder are plotted as dots in the x-y plane (FIG. 22.3). Dots from the more recently acquired data are less transparent to make the C-mode have a comet tail-like shape. Pubic bone information can be overlaid on the comet tail image.

Step 4: On-Target Indicator (Optional)

From the generated C-mode, it can be determined whether the bladder is centered enough or not. If it is well centered for a certain period of time, e.g., 2 seconds, an on-target indicator can be turned on (FIG. 22.4). The on-target indicator can be also used for triggering bladder volume calculating process.

Calibration Method Using Plate Target

Typical ultrasound bladder scanners use a single-element transducer that moves mechanically in a dome-shaped probe head. For this type of devices, precise calibration of transducer motions is optionally advantageous for accurate volume measurement. An ultrasound target with a known shape, e.g., spiral or string, in water tank is typically used for this purpose. One of the problems of the typical calibration method is that there could be a parallax issue. An embodiment of the present invention solves this problem and provides other benefits including smaller calibration fixture and better reliability by utilizing intensity information of the beam reflected from a plate target, instead of using the spiral/string target location/shape information.

Figure 23:
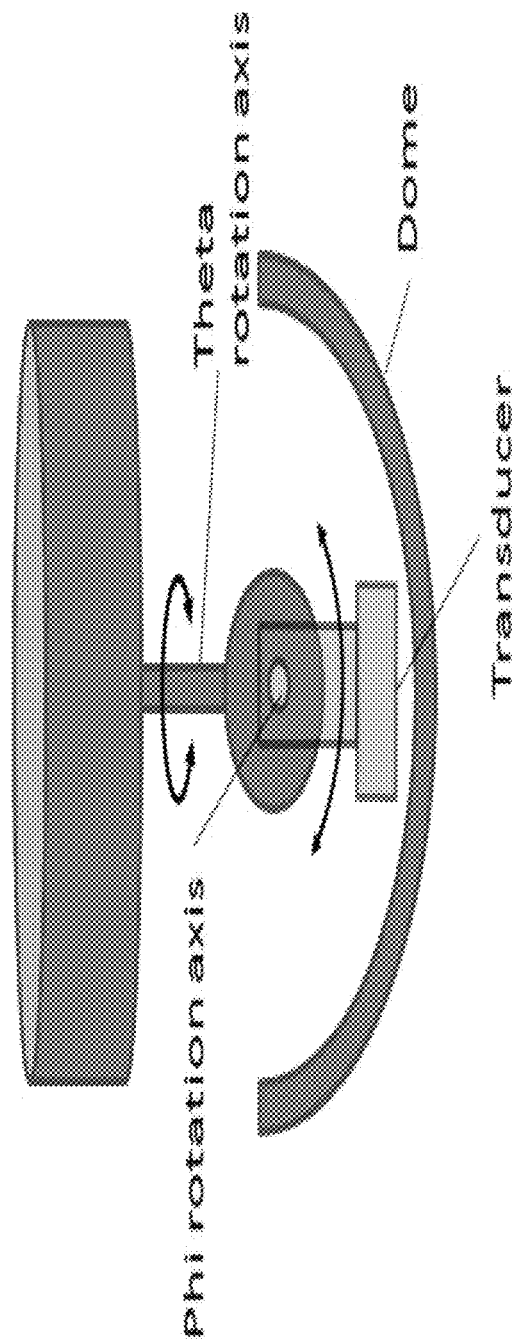

An embodiment of the present invention provides a method for abnormal transducer motion detection of a mechanical three-dimensional one-channel ultrasound probe used for bladder volume measurement. This type of probe has a moving transducer in the dome-shaped probe head filled with coupling/lubrication fluid such as mineral oil. In this probe, transducer motion is characterized by rotations about two axes, phi and theta, as shown in FIG. 23. As transducer motions can be inaccurate for several reasons, e.g., skew angles of phi/theta rotation axes, gear backlash, wear and tear, etc., it needs to be precisely measured and calibrated for accurate volume measurement, which has been commonly done using an external calibration target, e.g., spiral or string, immersed in a water tank.

One of the problems of the typical calibration method is that there could be a parallax issue. FIG. 24(a) shows a probe with a crooked transducer. In this case, ultrasound beam does not go straight down unlike the intention of the device. To compensate for this error, typical calibration methods try to match the location of a calibration target on the two ultrasound images obtained before and after 180-deg rotation about the theta axis. If the transducer is not crooked as in FIG. 24(b), the device can accurately find the phi angle that makes the beam go straight down. However, with a skewed transducer, actual calibration result is still not accurate due to the parallax error as shown in FIG. 24(c). With this parallax, desired calibration result in FIG. 24(d) is difficult to achieve. The parallax problem can be relieved if a calibration target is far from the transducer, but then poor lateral resolution of the ultrasound in the far field would affect the calibration accuracy, and calibration fixture could become too bulky.

As a new calibration method that does not have parallax problem, an embodiment uses a reflective plate target, e.g., metal surface, instead of a typical string or spiral target. By using the intensity information of the reflected beam from the plate target, instead of the target location information that is typically used, an embodiment provides a more accurate way of doing calibration without any parallax problem, as well as other benefits like smaller fixture and better reliability.

a. Parallax in calibration: An embodiment of the present invention uses a plate target that does not have parallax problem.

b. Bulky calibration fixture: Small fixture can be used for the plate calibration because a plate target can be very close to the probe. So, an embodiment enables use of several different types of calibration fixtures, e.g. a calibration cup or a small rubber block with a plate target in it, instead of traditional bulky water bath.

c. Small tolerance in probe—target alignment: A plate target doesn't have to be well aligned with the probe for calibration using the proposed method. This means plate calibration could be more reliable than traditional methods as some misalignment or an error in calibration fixture doesn't affect the calibration result.

A. Phi Offset Calibration

One of the main purposes of the calibration process is to estimate appropriate phi offset and firing delay values to make the orientation of the B-mode image correct. This can be done by comparing a beam peak intensity profiles with another one in the same scan plane after 180° theta rotation as shown in FIG. 25. For example, for a system that doesn't have any phi error, the maximum peak intensity angles in the first and second profiles, $\varphi_{peak1}$ and $\varphi_{peak2}$, respectively, would have the relationship, $\varphi_{peak1}=180°-\varphi_{peak2}$. For a system where actual phi angle of the beam is skewed by $\varphi_{offset}$ from the correct direction, two angles of maximum peak would meet the following equation: $2\varphi_{offset}=\varphi_{peak1}-(180°-\varphi_{peak2})$. By utilizing this relationship between peak intensity angles, phi offset can be calibrated through the following procedure:

Step 1: Collect ultrasound data (RF, IQ or B-mode) in a scan plane.

Step 2: Calculate the maximum ultrasound intensity profile from the data.

Step 3: Collect another ultrasound data in the same plane with the same phi motion after 180° theta rotation.

Step 4: Calculate the second maximum intensity profile from the second data.

Step 5: Estimate the phi angle difference between the two profiles. Peak detection, or cross correlation method for better precision, can be used after flipping the send profile.

Step 6: If the estimated phi angle difference is small enough, use the current phi offset/firing delay value for calibration. Otherwise, adjust the phi offset/firing delay according to the difference. If necessary, then repeat steps 1-6.

Figure 24:
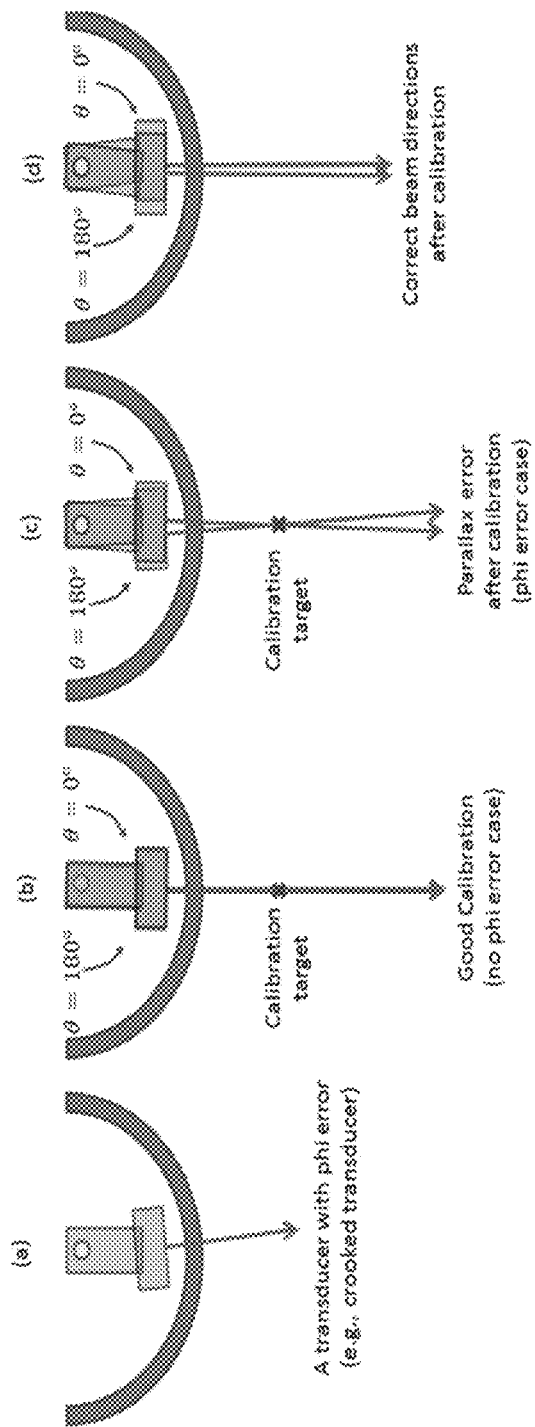

One of the virtues of the plate calibration is that the relationship between peak angles is valid regardless of the angle of the surface target, thus target can be skewed from the probe as in FIG. 24. So, plate calibration fixture including probe holder can be made more easily with less precision compared to typical ones.

B. Gear Backlash Calibration

Figure 26:
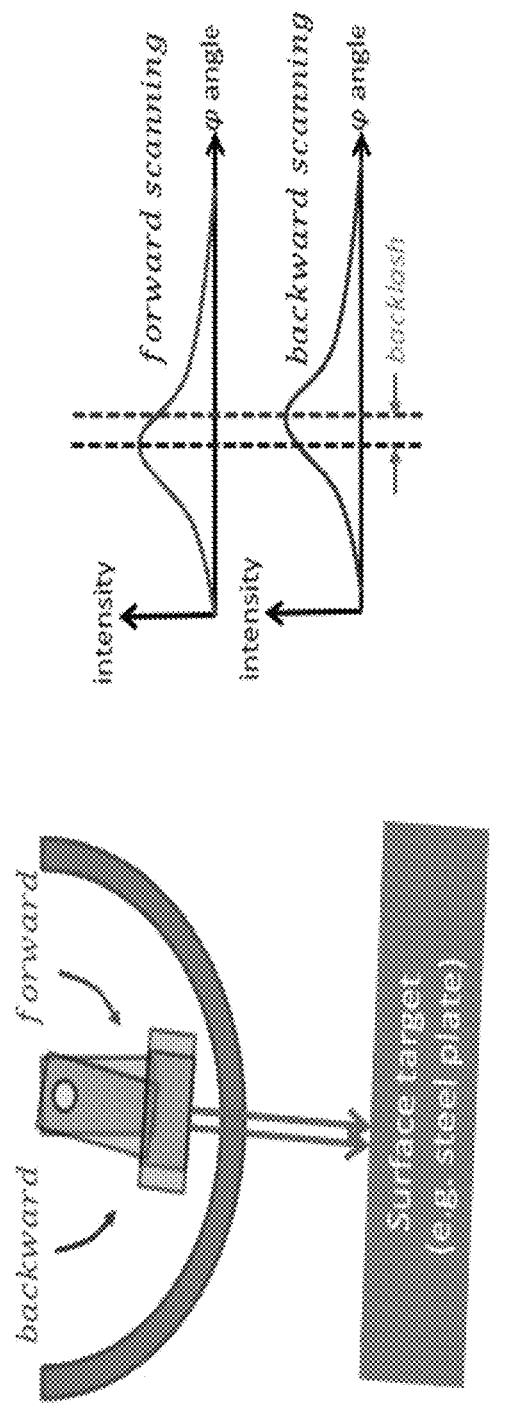

If a probe does a two-way scanning by rotating the phi motor in both directions, there could be small amount of misalignment between the forward and backward scanning mainly due to the gear backlash. This backlash can be estimated with a similar method used for phi offset estimation as shown in FIG. 26. In this case, two peak phi angles, $\varphi_{peak\_forward}$ and $\varphi_{peak\_backward}$ would meet the following equation: $2\varphi_{backlash} = \varphi_{peak\_forward} - \varphi_{peak\_backward}$. Detailed calibration procedure is as follows:

Step 1: Collect ultrasound data (RF, IQ or B-mode) in a scan plane with forward phi motion.

Step 2: Calculate the maximum ultrasound intensity profile from the data.

Step 3: Collect another ultrasound data in the same plane with backward phi motion.

Step 4: Calculate the second maximum intensity profile from the second data.

Step 5: Estimate the phi angle difference between the two profiles. Cross correlation of the two profiles can be used as an estimation method.

Step 6: If the estimated phi angle difference is small enough, use the current backlash value for calibration. Otherwise, adjust the backlash according to the difference. If necessary, then repeat steps 1-6.

C. Estimation of Skew Angle Perpendicular to the Scan Plane

While geometrical errors in the direction of phi motion (Type I error) can be compensated by adjusting phi offset/backlash, there is another type of error (Type II error) that is perpendicular to the scan plane. In reality, a geometrical error is likely to be a composition of these two different types of errors. The type II error is difficult to compensate physically by controlling the motor motion or firing delay, but information on the type II error can be used to detect a faulty probe or to compensate for bladder volume in software. With a plate target, the type II error can be estimated according to the following procedure:

Step 1: Collect ultrasound cone data (RF, IQ or B-mode) on a plate target with forward phi motion.

Among all the scanlines that covers a cone, at least one scanline is perpendicular to the plate target. (This is because the plate can be thought as a tangent plane of the cone. The scanline that crosses the point of contact is perpendicular to the plate target. The number of scanlines could be increased by interpolation to get a better angular precision.) However, there could be an exceptional case where a hole, like an eye of hurricane, that none of the scanlines passes through exists due to the type II error. In this case, none of the scanlines could be perpendicular to the plate target. To avoid this situation, the plate target needs be tilted from the surface seen straight from the probe. For example, if expected maximum type II error is 5 degrees, the plate target should be tilted by at least 5 degrees.

Step 2: Find a scan plane perpendicular to the plate. Then, find the relationship between the incidence angle and peak intensity.

The scanline that is perpendicular to the plate target can be found by finding the scanline that has the largest peak intensity. The scan plane that contains the scanline should be perpendicular to the plate. In this scan plane, thanks to the perpendicularity, we can derive the relationship between the incidence angle (phi angle) and the peak intensity from the plate target.

Step 3: Collect ultrasound data in a scan plane, then collect another one in the same plane after 180-deg theta rotation. In this case, make sure that plate target is tilted at least as much as expected maximum type II error from the surface seen straight from the probe in the direction perpendicular to the scan plane.

Instead of this separate data collection step, we could make the first scan plane overlap the last scan plane with 180-deg theta angle difference in Step 1 for convenience. Or, the data used in the phi offset calibration can be used again if probe and plate target have not moved.

Step 4: Calculate incidence angles of the maximum intensity beam for two plane data acquired in Step 3 using the incidence angle—peak intensity relationship derived in Step 2. Calculate type II error by dividing the difference between the incidence angles by two.

If there's no type II error, two planes should overlap perfectly, then two incidence angles should be the same after phi offset calibration. In the presence of a type II error, two planes have an angular gap that causes differences between the two incidence angles. As we tilted the target more than the maximum type II error in Step 3, two scan planes are tilted into the same direction about the scan plane. Thus, type II error can be calculated simply subtracting one incidence angle from the other followed by a division by two.

D. Simulation Example

To show an example of the proposed method, a 13-plane peak intensity profile data were simulated using Matlab. The first plane overlaps the $3^{th}$ plane with 180-deg theta angle difference. In this simulation, we assumed that plate target is intentionally skewed by 5 degrees towards southeast, and the probe has 3 degrees of phi offset and one degree of type II error.

Figure 27:
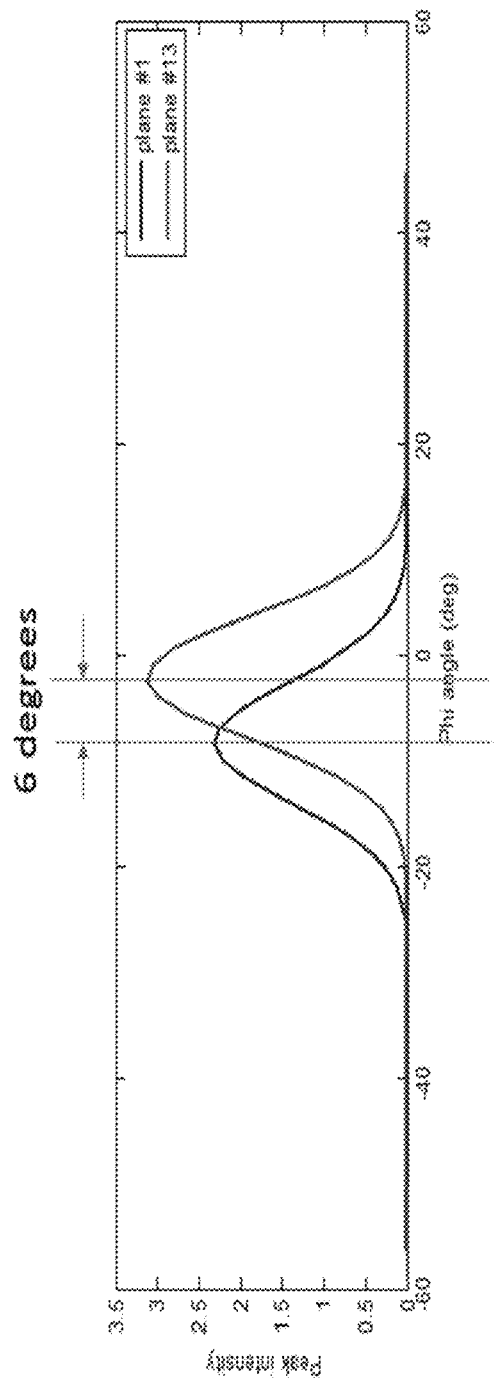

FIG. 27 shows two intensity profiles in plane #1 and #13 (flipped for comparison). The 6-deg difference between the two peaks caused by the 3-deg phi offset is clearly observable in the figure. For accurate estimation of the phi offset, intensity profiles can be interpolated to improve the angular resolution. Note that peak intensities are different each other. This implies that type II error is not zero in this case. Backlash was not tested in this simulation, but it can be estimated using the same principal to the phi offset estimation.

Figure 28:
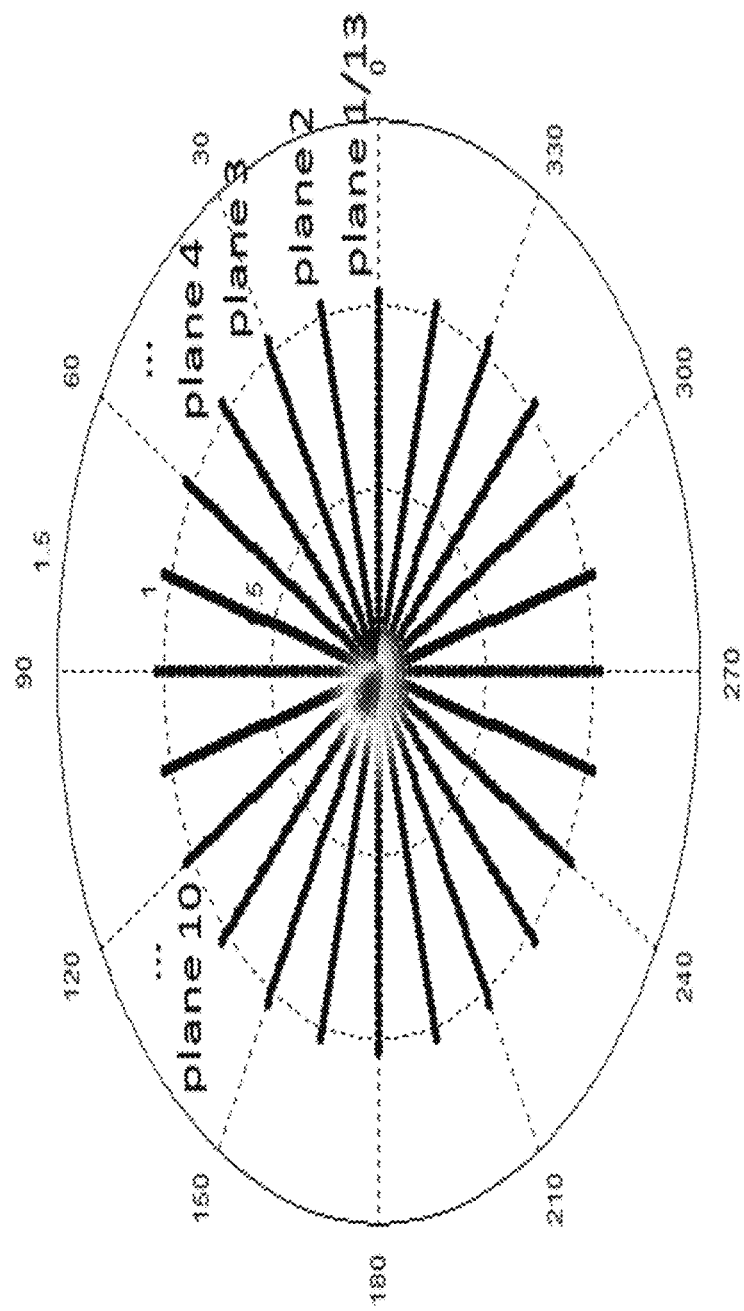
Figure 29:
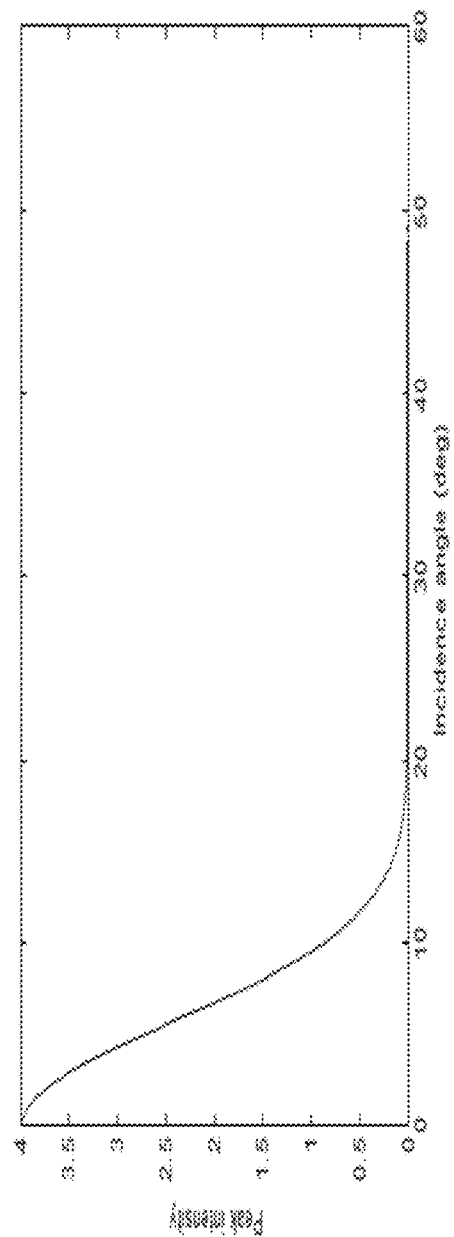
Figure 30:
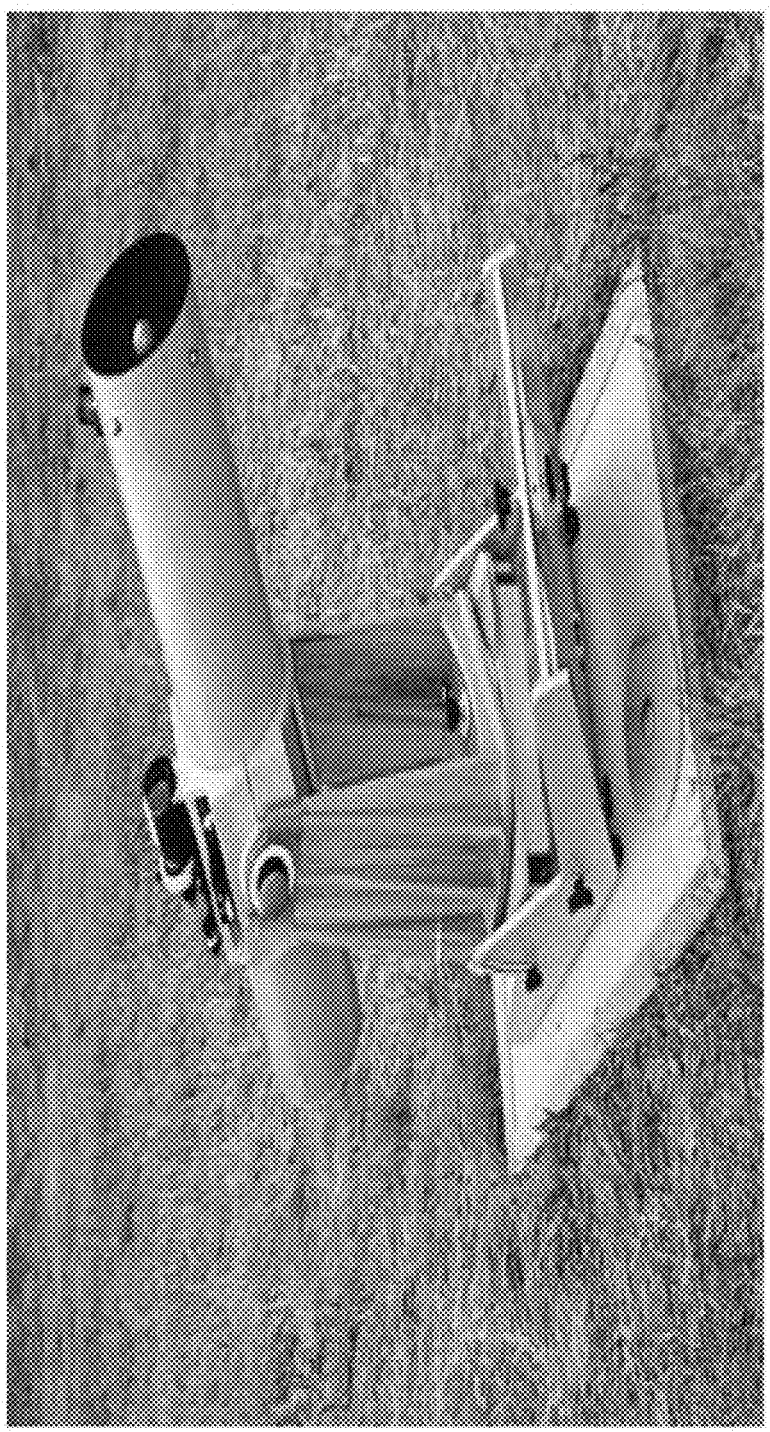
Figure 31:
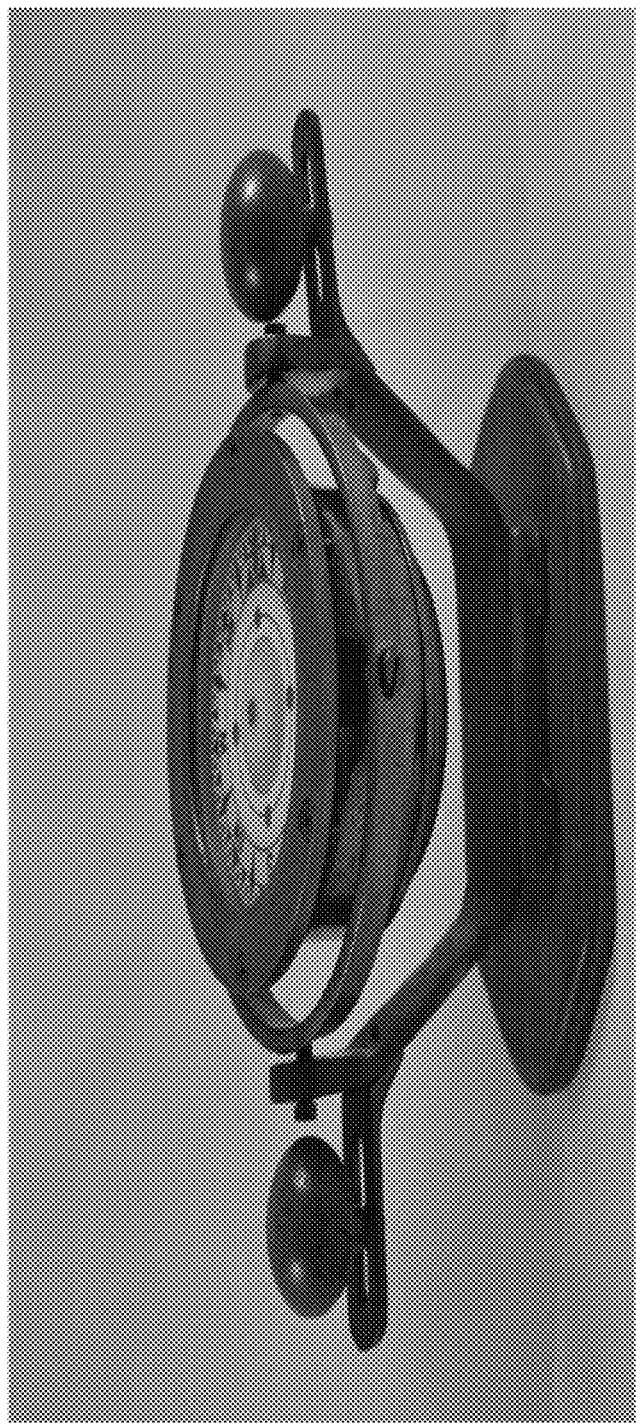
Figure 32:
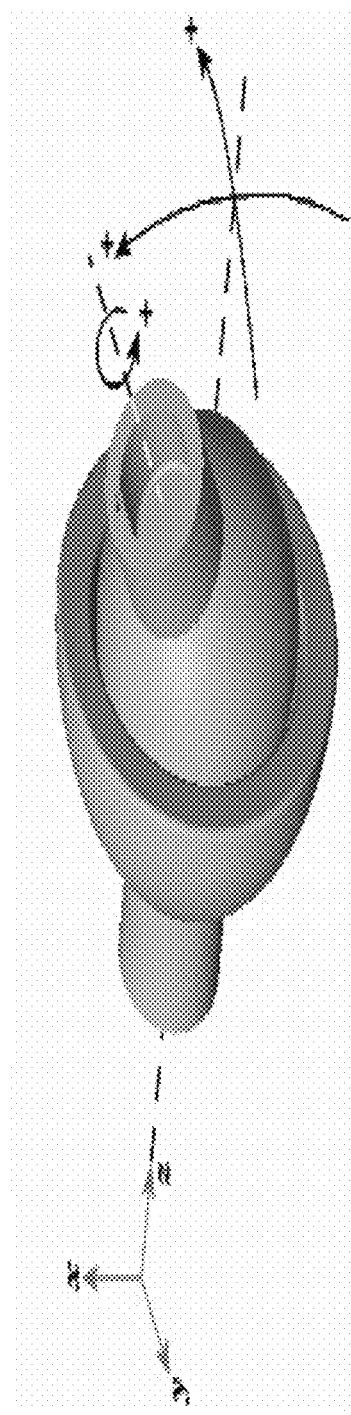
Figure 33:
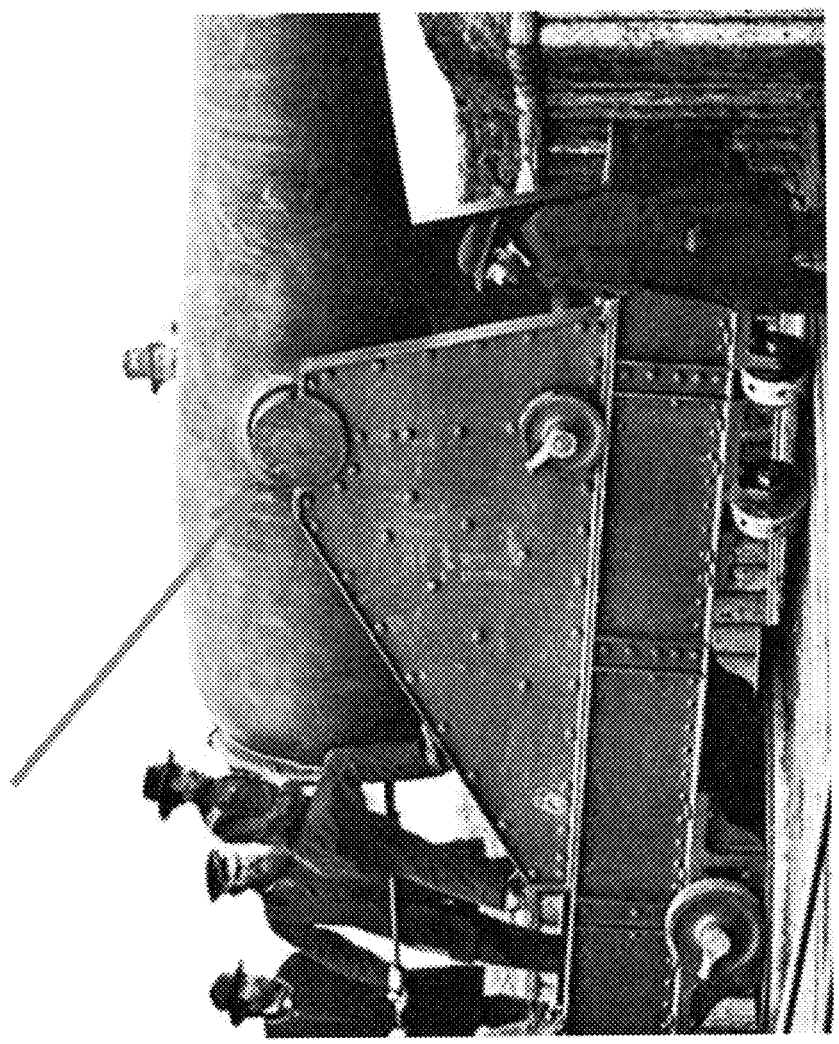
Figure 34:
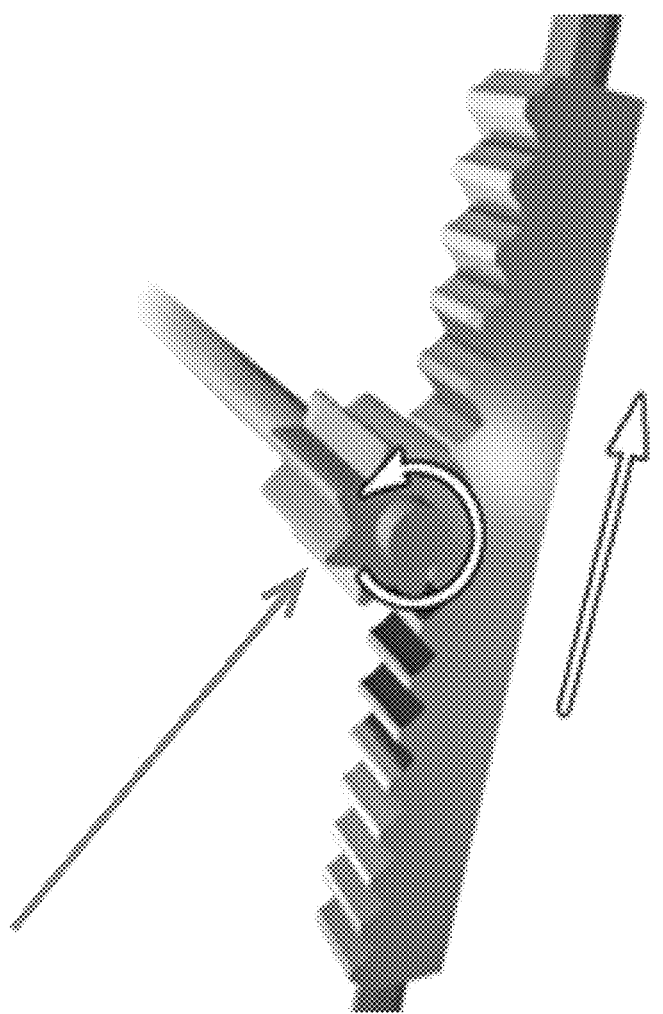
Figure 35:
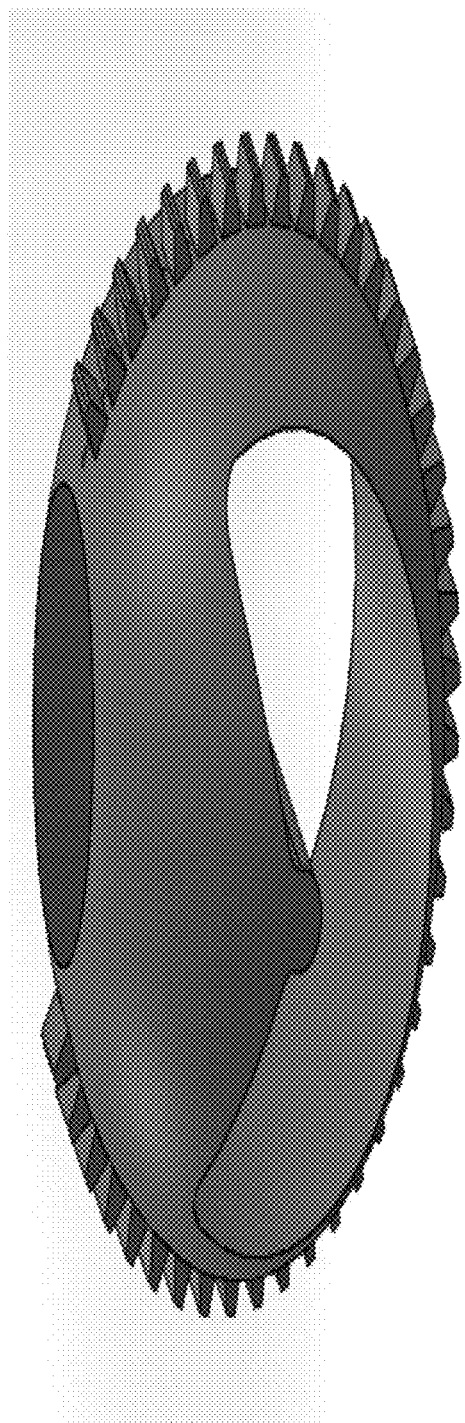
Figure 36:
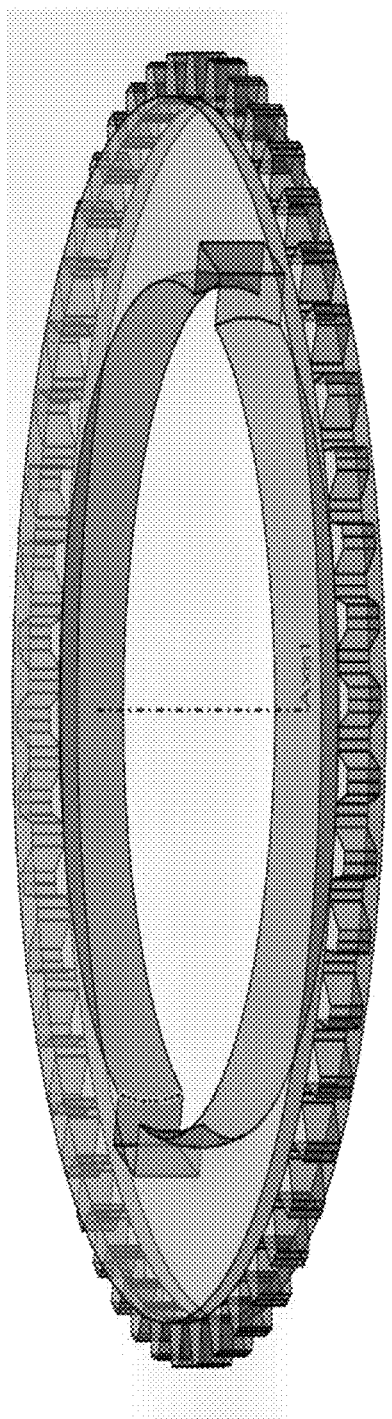

FIG. 28 shows peak intensities of reflected beam at 1040 scanline locations (80 scanlines×13 planes). In this figure, the scanline with the maximum intensity is on the $10^{th}$ plane. So, we can assume that the $10^{th}$ plane is perpendicular to the plate target. (For better accuracy, we can actually interpolate the $10^{th}$ plane with the $11^{th}$ plane, to find the plane exactly perpendicular to the plate.) From the peak intensity profile in this plane, we can derive the relationship between the beam incidence angle and peak intensity as shown in FIG. 29. This profile was smoothed with interpolation for better accuracy.

In FIG. 27, peak intensities in planes 1 and 13 were 2.32 and 3.16, respectively. These values correspond to the incidence angles of 6.05 and 4.03 degrees in FIG. 6, respectively. By dividing the difference between the angles by two, we can get the type II error; i.e., (6.05−4.03)/2=1.01 degree. This value well matches to the simulation parameter, type II error of one degree.

Ball-and-Socket Hemispherical Scan Mechanism

Figure 37:
Figure 38:
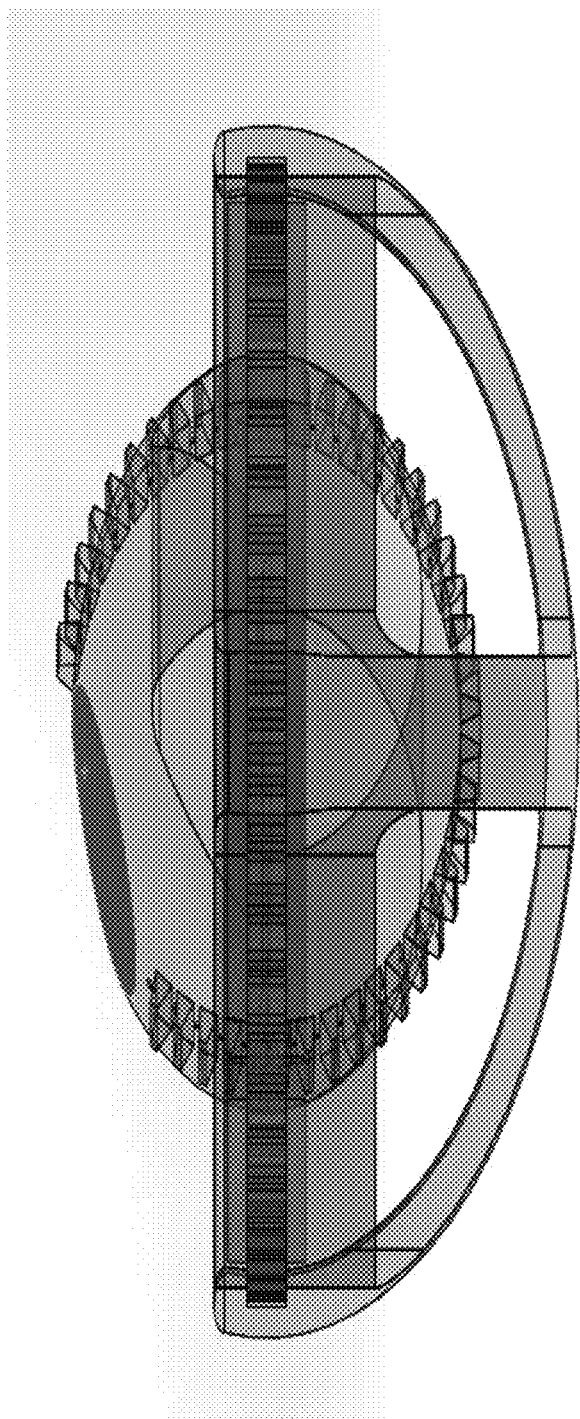
Figure 39:
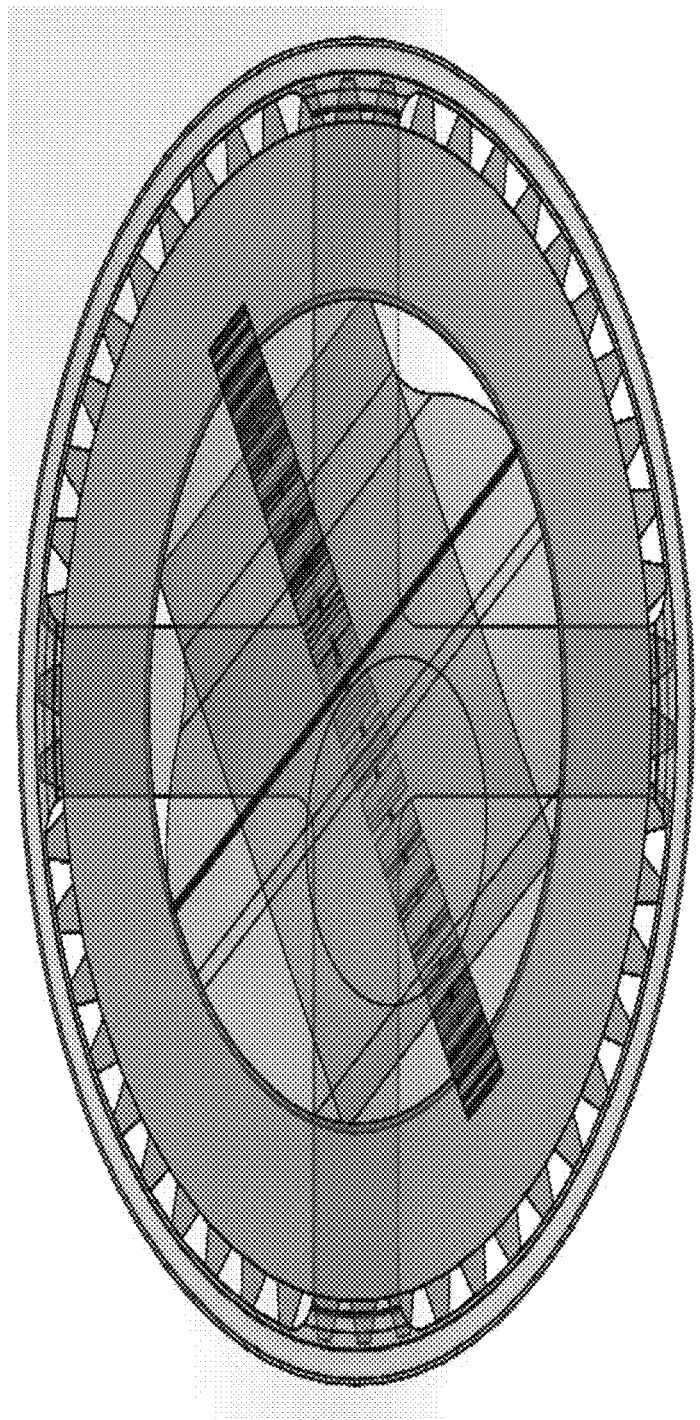
Figure 40:
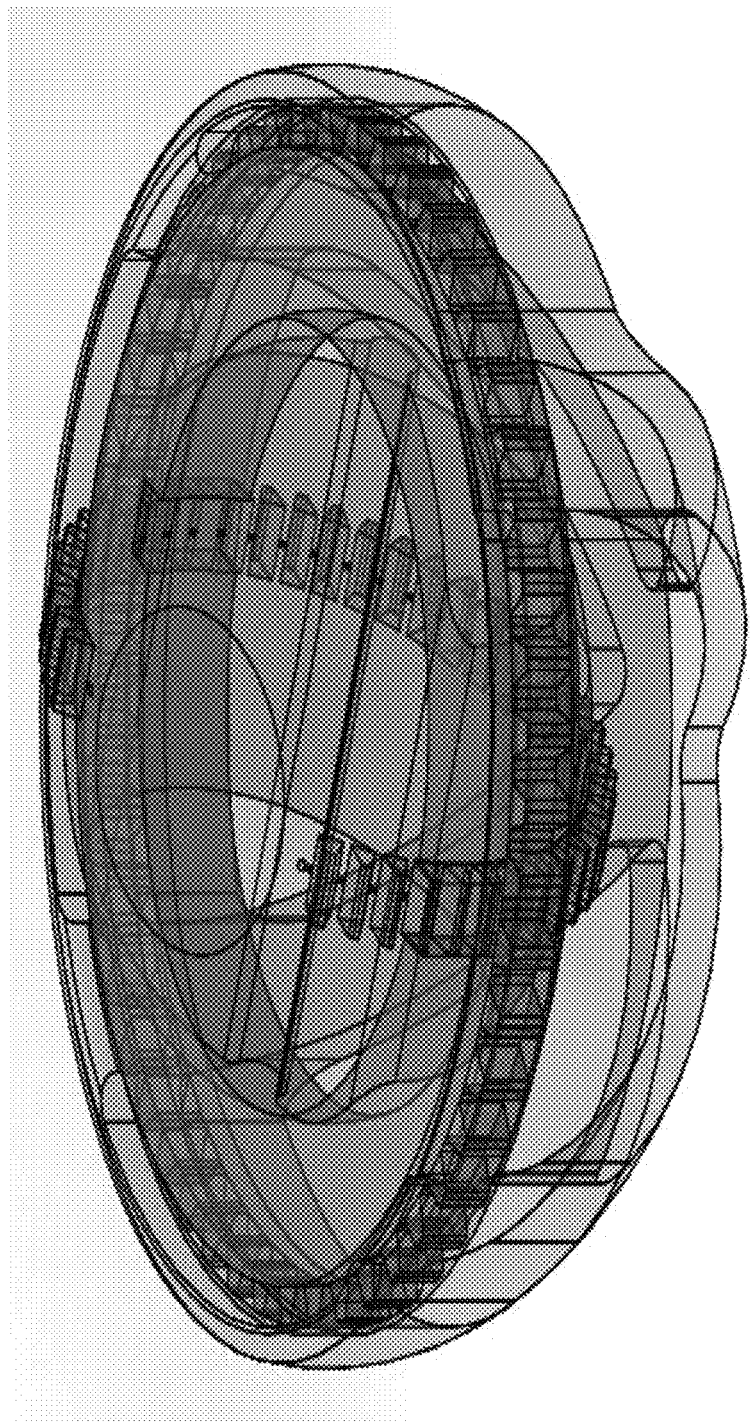

An embodiment includes a reliable hemispheric scan mechanism for use in, for example, the Bladderscan and Aortascan product line.
1. Description of an Embodiment:
a. Purpose
This mechanism was invented for the purpose of supporting and pointing directive sending and receiving devices in various desired directions, thus mapping out a two dimensional region of interest, within a hemispherical region.
b. Drawings
An embodiment of the invention is illustrated in FIGS. 30-38 below. For clarity, motors and small pinion gears (FIG. 34) are not shown.
c. Description of the Parts
An embodiment of the invention consists of three principal components, a spherical "eyeball" transducer holder with integral "latitude" gear teeth (FIG. 35), a gimbal ring with integral "longitude" gear teeth (FIG. 36) and a support frame with a longitude ring groove (FIG. 37).
The longitude motor (for clarity, not shown) is attached to the support frame and the latitude motor (for clarity, not shown) is attached to the gimbal ring. The inside surface of the gimbal ring is formed with a spherical contour. The transducer holder sphere is held in place within the gimbal ring component. It has an external surface with a spherical contour matching that of the gimbal ring.
When the transducer holder and the gimbal ring are driven by two electric motors, through pinion gears (for clarity, not shown), a directive transducer may be pointed in any desired direction within a hemispherical region.
d. Use
In operation, two motors independently and simultaneously move and position the inner transducer holder and the outer gimbal ring so as to point a transducer toward any latitude and longitude coordinate, within a hemispherical region, which the application requires.
e. Features
Hemispherical scan mechanisms typically use two motors and two associated gear mechanism in order to point a transducer device in various directions within a hemispherical region. Two common prior art mechanisms are the alt-azimuth mount often used to support telescopes (FIG. 30) and the gimbal mount (FIG. 31) often used to support compasses and gyroscopes.
The alt-azimuth and gimbal mount have deficiencies which an embodiment of the invention circumvents. In particular, the prior art devices are large, delicate and complex. This makes them comparatively heavy, expensive, less reliable and less tolerant of damage through misuse.
An embodiment of the invention circumvents these deficiencies by combining two novel ideas:
  1. It uses a ball-and-socket support mechanism (FIG. 32) instead of the more common trunion bearings (FIG. 33)
  2. It integrates the two required drive gears into their associated gimbal ring and transducer holder parts.
Features
As a result of the novel features, my invention has the following advantages over hemispherical scanning mechanisms found in the prior art.

it requires relatively few components
  the few components are relatively easy to fabricate
  the few components are individually rugged and thus damage resistant
  the few components are inexpensive to fabricate
  the few components do not extend very far vertically or laterally. This makes the mechanism, as a whole, compact and rugged.
  the few components do not extend very far vertically or laterally. This allows space for a shock mount spring feature
  the few components do not extend very far vertically or laterally. This allows space for more electronic circuitry in a probe hand piece
  the few components do not extend very far vertically or laterally. This allows space for better electrical shielding of electronic circuitry in a probe hand piece
  many spatial directions can be sampled within a hemisphere, without the transducer electrical connection cable being repeatedly wrapped and unwrapped around one or more motor shaft axis.
  The electrical connection to the transducer device can be made relatively short, thus reducing signal interference opportunities
f. Testing
A computer CAD model of an embodiment has been created that allows examination of the relative motion of the various components, as they would move in actual use.

Spherical Spiral Path Scan Mechanism

2. Description of an Embodiment:
  a. Purpose
  An embodiment of the invention achieves the purpose of supporting and pointing directive sending and receiving devices in various desired directions, thus mapping out a two dimensional region of interest, within a hemispherical region.
  b. Drawings
  An embodiment of the invention is illustrated in FIGS. 41-49 below.
  c. Description of the Parts
  An embodiment of the scanning mechanism consists of five principal components, which when driven by a motor, move a directive transducer so as to point in many directions within a hemispherical region.
  The components are: a gimbal mount, with 1) inner ring and 2) outer shell, to support the transducer holder 3) a cup, with spiral grooves to guide the transducer pointing direction along a spiral path 4) a transducer holder, with a short pin extending down from the holder body that engages with a spiral groove in the grooved cup body to force pointing of the transducer along a defined spiral path 5) a slotted cup to move the spiral groove guided pin in a spiral direction 6) an optional shuttle feature (not shown in a figure) that allows the pin to cross spiral grooves at an acute angle without chance of changing direction at the groove intersections.
  d. Use
  In operation, motor torque is applied to a shaft that extends downward from the slotted cup component. This torque rotates the slotted cup. As the slotted cup rotates, the captured pin feature, extending downward from the bottom of the transducer holder, is forced to follow a spiral slot containing the captured pin. As the captured pin moves within the spiral slot, the transducing device is then necessarily pointed in a direction away from the pin and co-axial with its axis. In this manner, a spiral shaped scan path is traveled by any energy beam being sent and-or received by the transducer device mounted in or on the mechanism inner gimbal ring.

e. Novel Features

Hemispherical scan mechanisms typically use two motors and two associated gear mechanism in order to point a transducer device in various directions within a hemispherical region. An embodiment of the invention, not described in the prior literature, points a transducer mechanism in many directions covering a region of interest within a hemisphere, without using any gear mechanisms. Also, by employing a spiral scan path, the mechanism may require only one motor to scan many points, in two spatial co-ordinates, within a hemispherical region.

The spiral path scan plan is useful because the method substantially shortens the angular path that the mechanism must traverse, in order to scan a grid of points, in a hemispherical region. Drastically shortening the angular scan path allows a much faster scan rate and-or a large reduction in mechanism power consumption.

An additional novel aspect of an embodiment is the optional incorporation of a crisscrossed spiral groove feature. The crisscrossed groove allows the spiral transducer beam pointing path to spiral both outward, from the center region, and inward, from the perimeter region, without changing direction or speed of rotation of the rotating elements. This allows maintenance of a high angular scan speed, while simultaneously reducing drive power requirements.

f. Features

As a result of the novel features, an embodiment of the invention has the following features distinguishable over hemispherical scanning mechanisms found in the prior art.
  it has relatively few components
  the few components are relatively simple in form
  the few components are individually rugged and thus damage resistant
  the few components are inexpensive to fabricate
  the few components do not extend very far above the drive motor. This makes the mechanism, as a whole, compact and rugged.
  the few components do not extend very far above the drive motor. This allow space for a shock mount spring feature
  the few components do not extend very far above the drive motor. This allow space for more electronic circuitry in a probe hand piece
  the few components do not extend very far above the drive motor. This allow space for better electrical shielding of electronic circuitry in a probe hand piece
  use of only one motor reduces cost
  use of only one motor reduces size
  use of only one motor reduces weight
  for a given number of spatial sample points, the total spiral scan path length is short. This allows sampling of many spatial directions in a very short time.
  fast scanning times reduce motion artifact
  fast scanning times allow smooth real-time scan imaging
  the spiral scan path does not impose frequent acceleration and deceleration of the transducer device. This reduces motor power.
  the spiral scan path does not impose frequent acceleration and deceleration of the transducer device. This reduces mechanism vibration
  the spiral scan path does not impose frequent acceleration and deceleration of the transducer device. This reduces mechanism wear and tear, thus enhancing reliability.
  many spatial directions can be sampled within a hemisphere without the transducer electrical connection cable being repeatedly wrapped and unwrapped around one or more motor shaft axis.
  The electrical connection to the transducer device can be made relatively short, thus reducing signal interference opportunities
  If axial symmetric transformer primary and secondary windings are used to couple transducer signals into and-or out of the rotating sub-assembly, a crisscross spiral groove feature may be used. The crisscross spiral groove feature provides the opportunity to hugely increase scanning speed while, at the same time, reducing drive power requirements.

g. Testing

A computer CAD model has been created that allows examination of the relative motion of the various components, as they would move in actual use.

Figure 41:
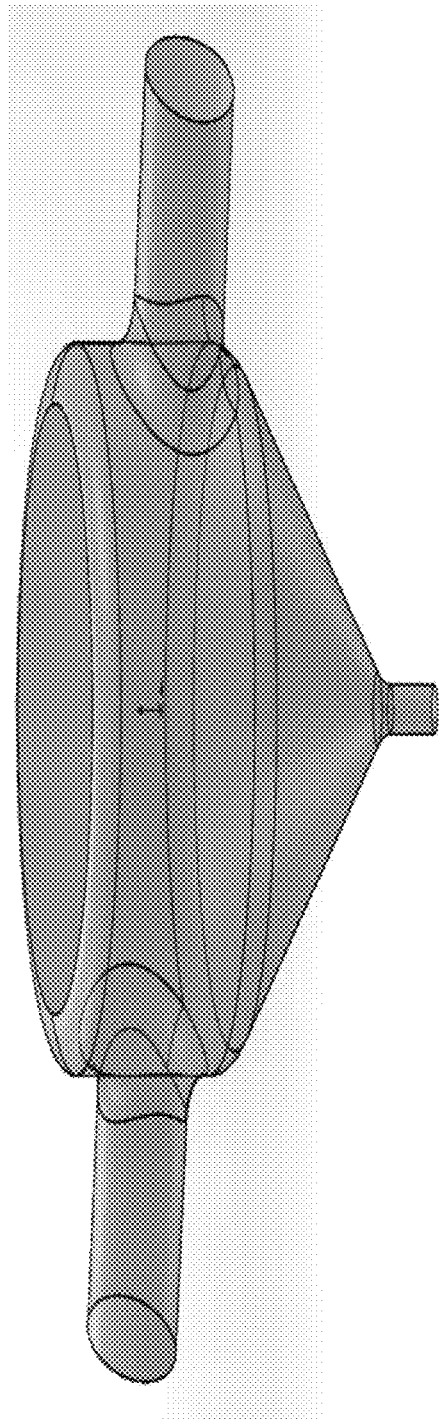

FIG. 41—Transducer holder with indexing groove following pin

Figure 42:
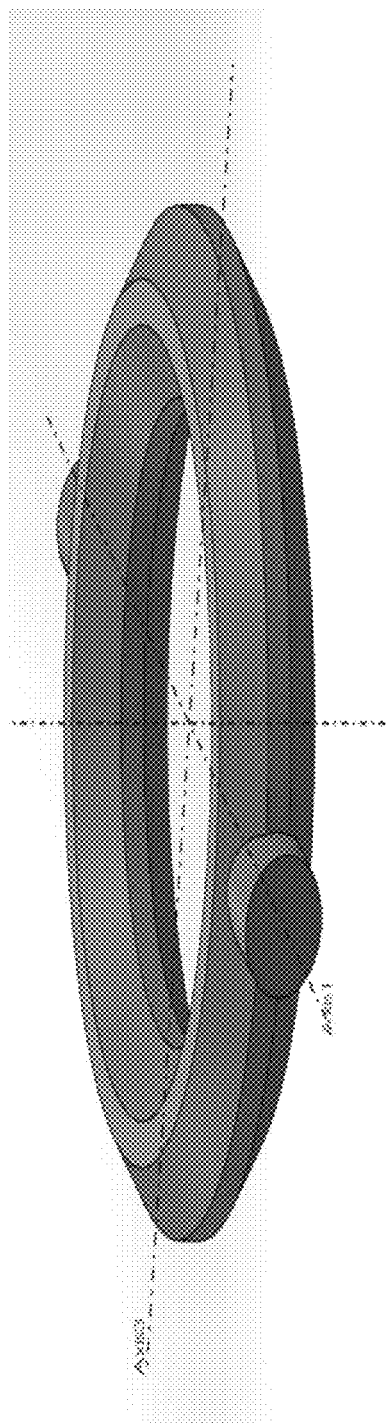

FIG. 42—Inner Gimbal Ring

Figure 43:
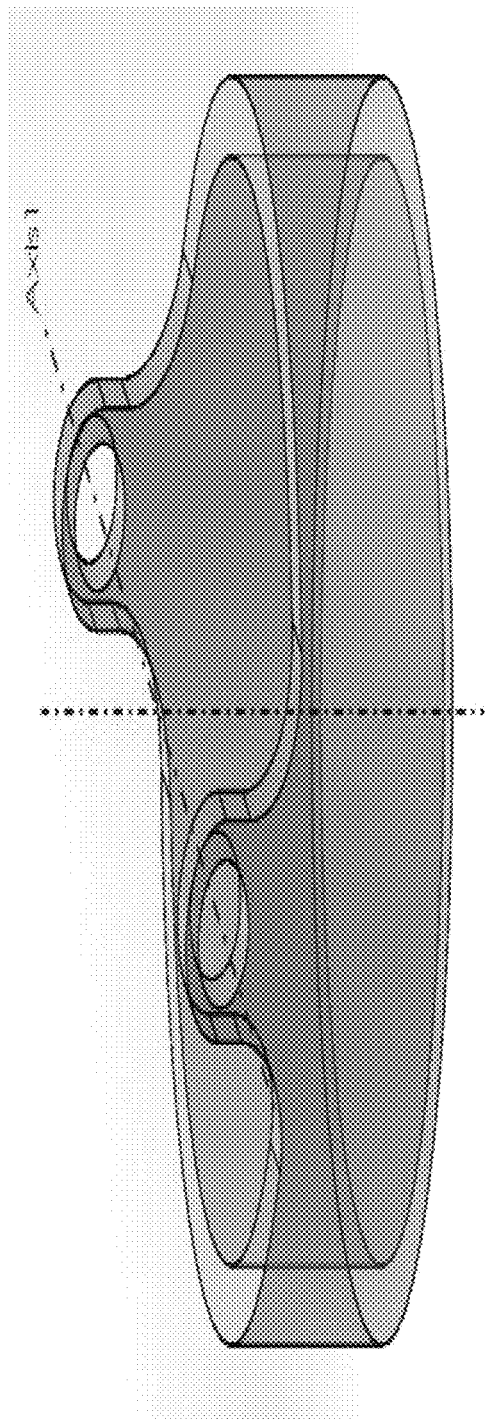
Figure 44:
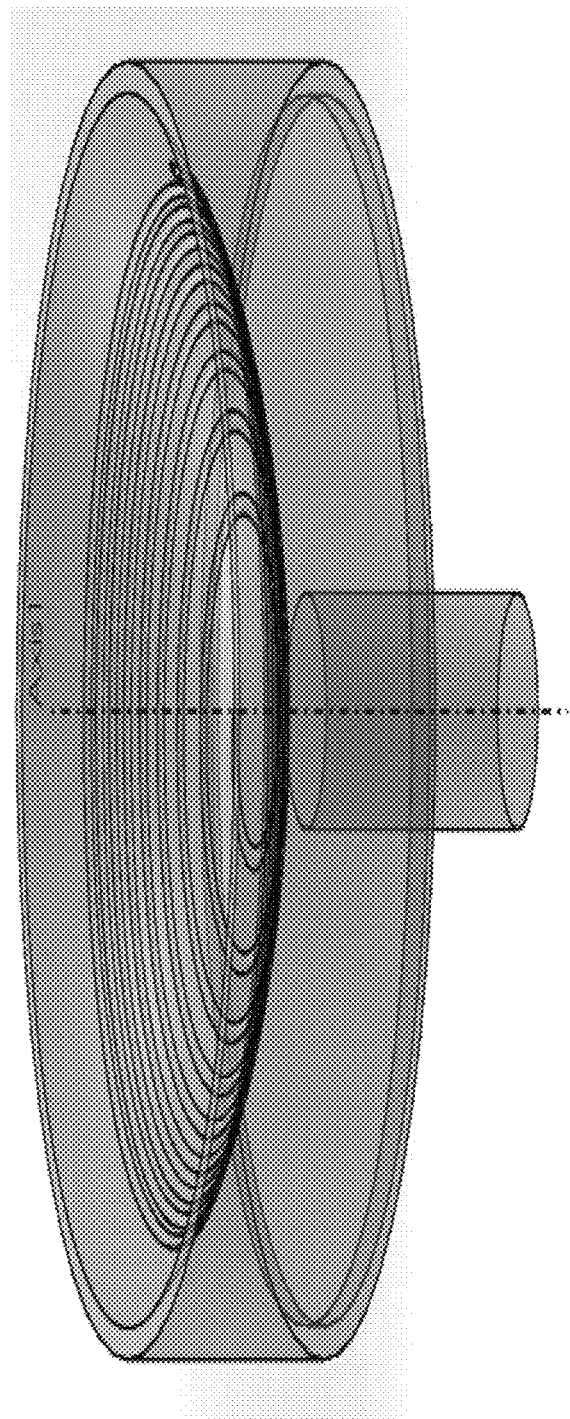
Figure 45:
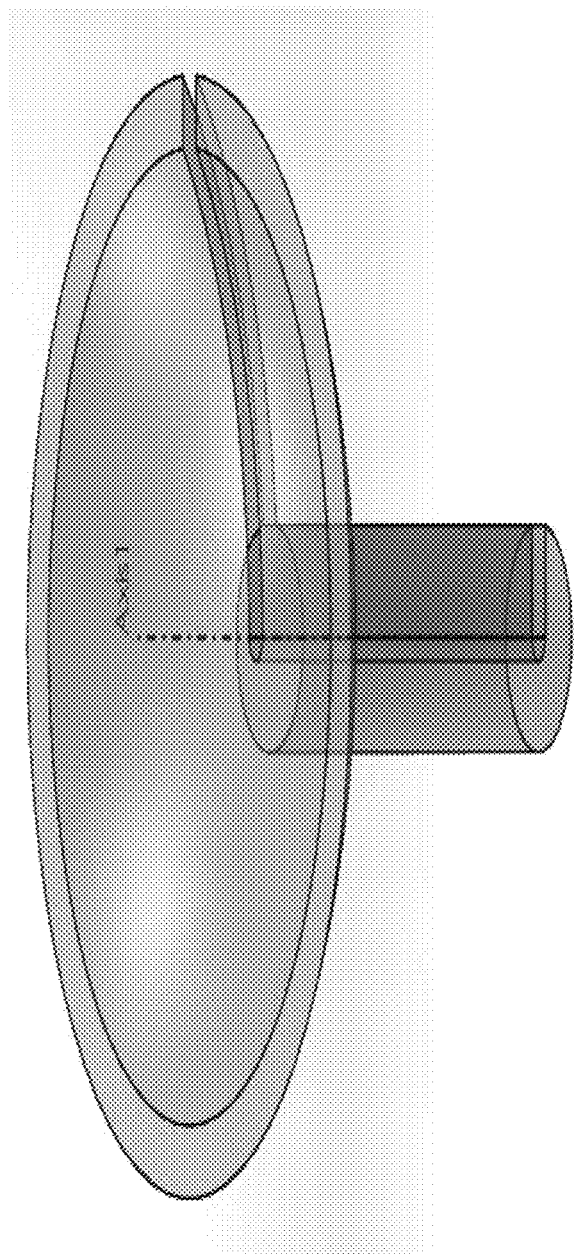

FIG. 43—Outer Gimbal Yoke

FIG. 44—Groove Cup

FIG. 45—Slot Cup

Figure 46:
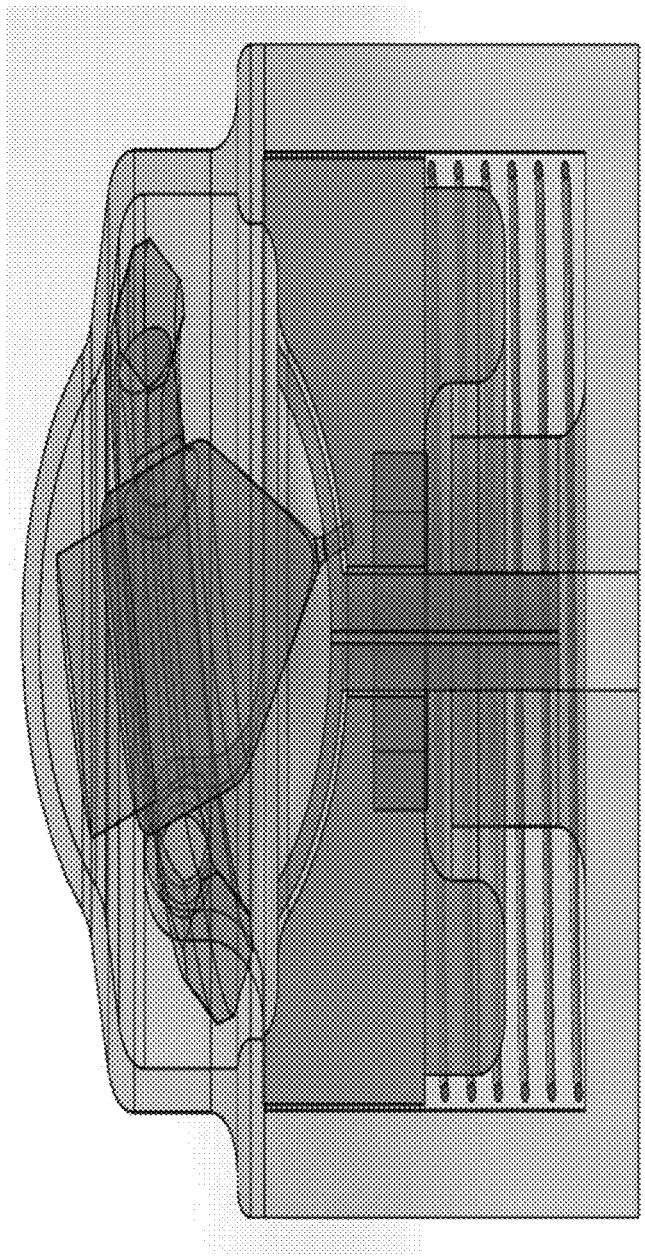

FIG. 46—Mechanism Cross Section

Figure 47:
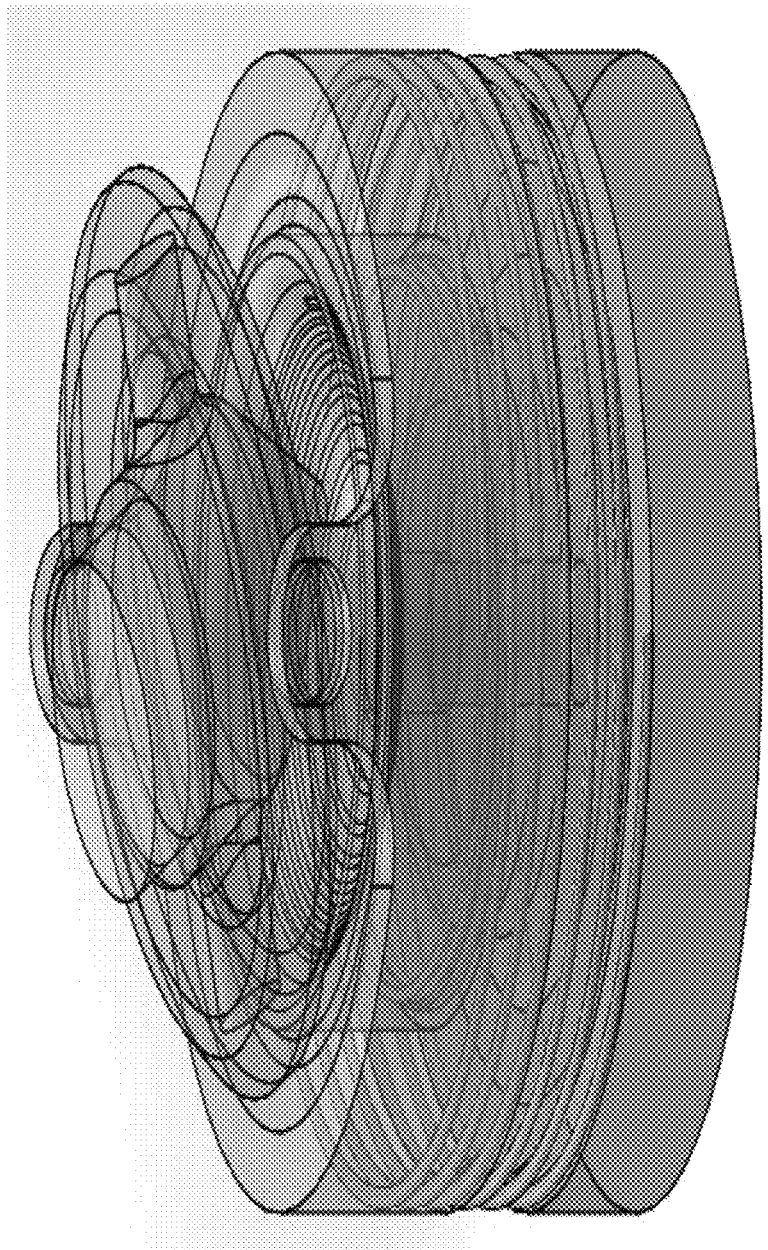

FIG. 47—Mechanism Isometric View

Figure 48:
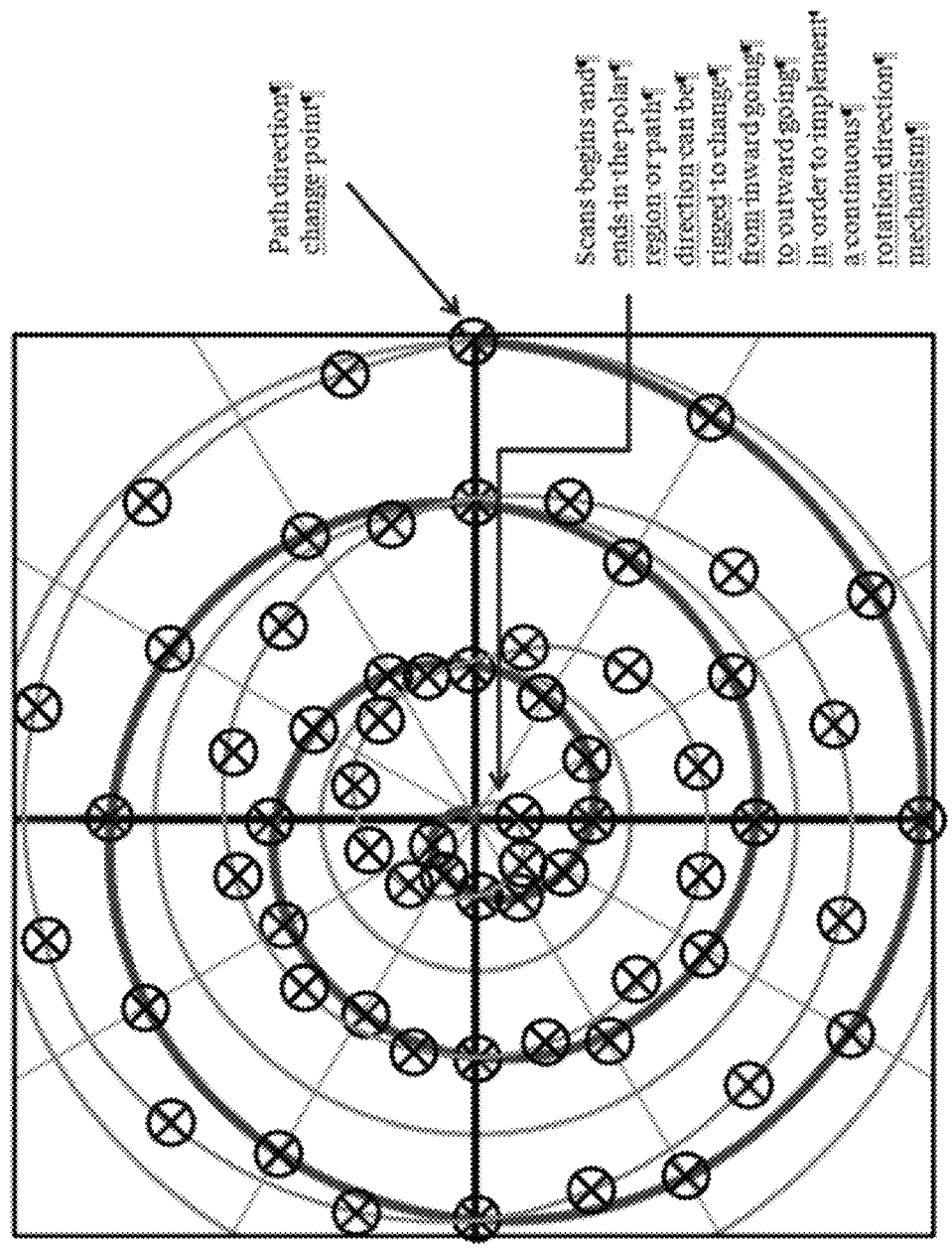
Figure 49:
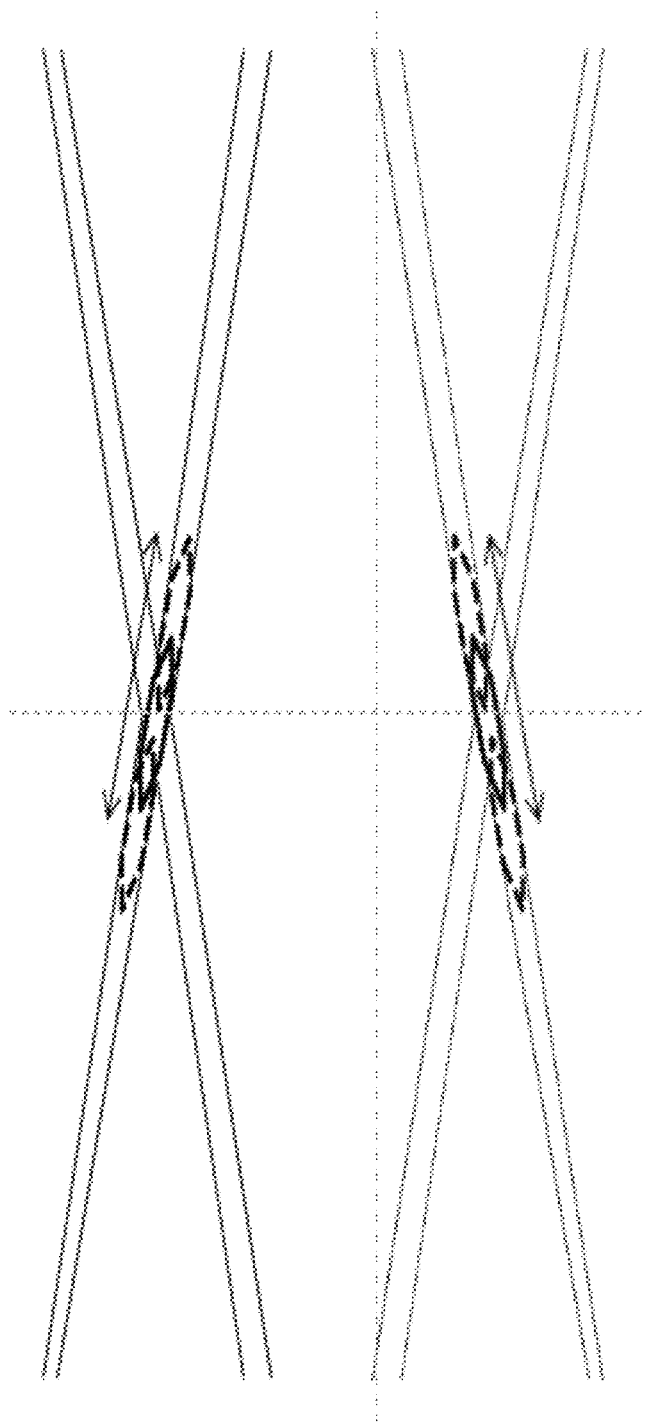
Figure 50:
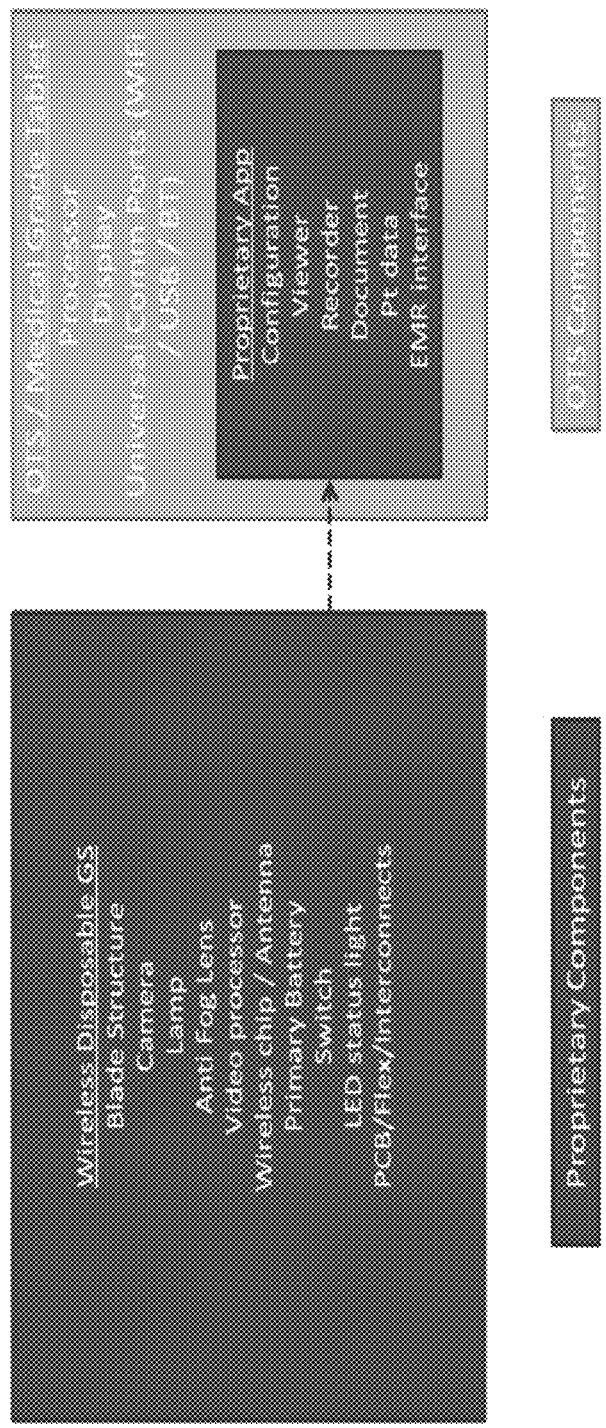
Figure 51:
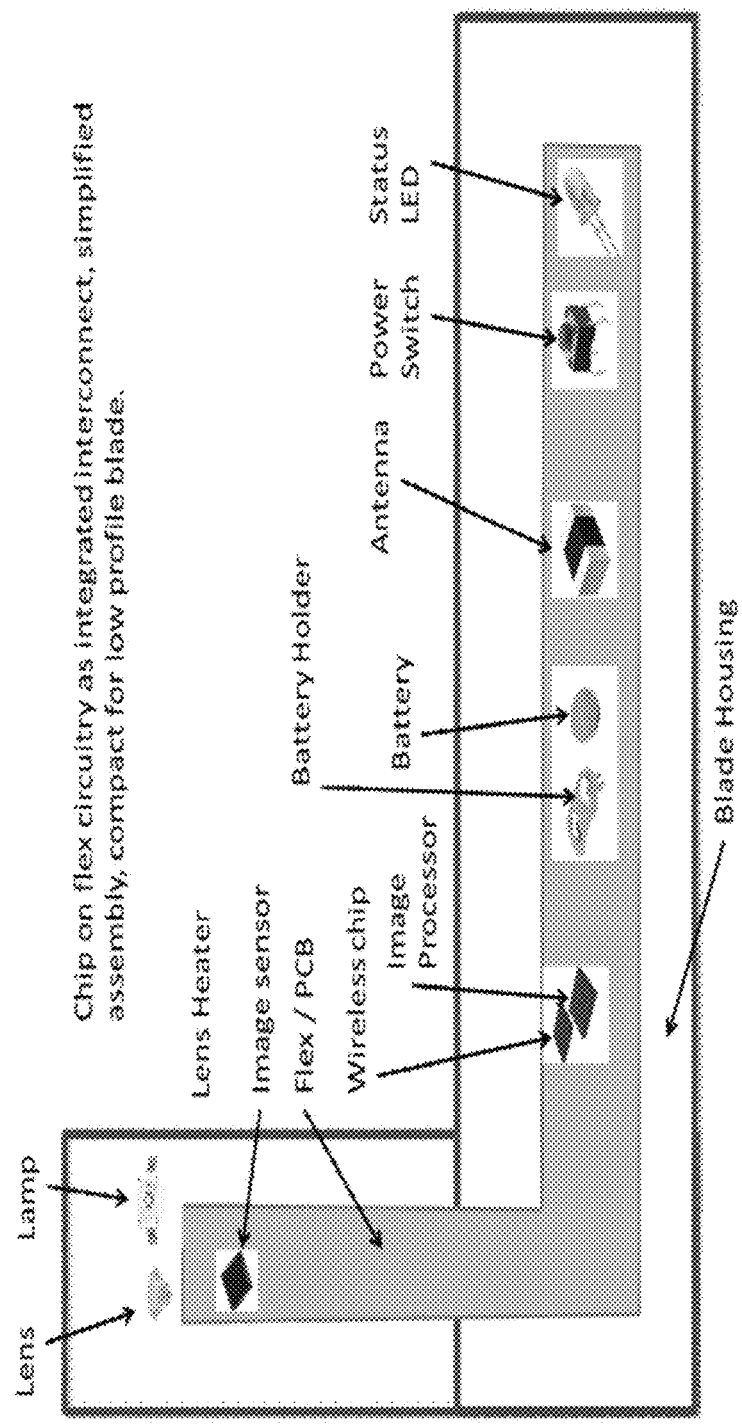

FIG. 48—Top view of a crisscross spiral scan path

An oblong groove follower won't "de-rail" or follow the wrong path at a groove crossing point. Any hysteretic "backlash" can be calibrated out FIG. 49—Oblong groove following pin maintains travel direction Wireless Disposable Video Laryngoscope with Interface to Generic Computing Display An embodiment of the invention is a single patient use disposable video laryngoscope blade that communicates wirelessly and displays images on a generic tablet computer (or other device) executing proprietary application software. This architecture could disrupt the laryngoscope product topology by reducing both the system capital cost and complexity of use and maintenance. In this system architecture, the display component would not be a proprietary, dedicated device, but instead leverage existing generic mobile computing devices in the hospital environment. There is recent enabling regulatory precedent for a tablet to be treated as office equipment, and only the application software to be registered as a medical device.

Optionally advantageous attributes of an embodiment that enable this technology include:

1. Wireless communications protocol that can stream video in real time with limited delay or interruptions in signal transmission to facilitate intubation procedure.

2. Lower power wireless communication protocol allows device to operate on a single primary battery, without charging or wired power connection.

3. Prolific communications protocol that enables medical device to display on commercially available computing displays without the need for a dedicated monitor component of the medical device.

4. Reliable wireless communications protocol and band between medical device and the computer.

5. Rapid pairing method to link the medical device and that display, such as scanning a bar/QR code on the medical device package, RFID tag, or NFC tag in order to exclusively associate the medical device with the display.

6. Low cost chip on flex circuitry to enable low cost of goods sold device with a target cogs of $12-15.

7. A latching power button to ensure the medical device is not allowed for reuse.

This architecture could disrupt the laryngoscope product topology by reducing both the system capital cost and complexity of use and maintenance.

Reduces cost
  No dedicated monitor, no rechargeable battery, no charger, no stand, no cables
Reduces maintenance
  No charging or management of state of charge, no sterilization between uses, reduced ER equipment footprint From the foregoing, it will be appreciated that specific embodiments of the personalized feed system have been described herein for purposes of illustration, but that various modifications may be made without deviating from the spirit and scope of the invention. Accordingly, the invention is not limited except as by the appended claims.

What is claimed is:

1. A method of calibrating an ultrasound scanner having a transducer that rotates about a first phi axis and a second theta axis, the phi axis being perpendicular to the theta axis, the method comprising:
  collecting from a reflective planar target first ultrasound data in a scan plane by rotating the transducer about the phi axis;
  calculating a first maximum peak intensity phi angle from the first ultrasound data;
  rotating the transducer 180° about the theta axis;
  collecting from the reflective planar target second ultrasound data in the scan plane by rotating the transducer about the phi axis;
  calculating a second maximum peak intensity phi angle from the second ultrasound data;
  determining a difference between the first and second maximum peak intensity phi angles; and
  setting a phi offset value for the ultrasound scanner based on the determined difference.

2. The method of claim 1, wherein the target is metallic.

3. The method of claim 1, wherein collected data is B-mode data.

4. A method of calibrating an ultrasound scanner having a transducer that rotates about a first phi axis and a second theta axis, the phi axis being perpendicular to the theta axis, the method comprising the steps of:
  collecting from a reflective planar target first ultrasound data in a scan plane by rotating the transducer about the phi axis in a first direction;
  calculating a first maximum peak intensity phi angle from the first ultrasound data;
  collecting from the reflective planar target second ultrasound data in the scan plane by rotating the transducer about the phi axis in a second direction opposite to the first direction;
  calculating a second maximum peak intensity phi angle from the second ultrasound data;
  determining a difference between the first and second maximum peak intensity phi angles; and
  setting a phi offset value for the ultrasound scanner based on the determined difference.

5. The method of claim 4, wherein the target is metallic.

6. The method of claim 4, wherein collected data is B-mode data.

7. The method of claim 1, wherein setting the phi offset value for the ultrasound scanner comprises:
  determining whether the difference between the first and second maximum peak intensity phi angles is less than a threshold.

8. The method of claim 7, wherein setting the phi offset value further comprises:
  setting the phi offset value for the ultrasound scanner to a current phi offset value, in response to determining that the difference between the first and second maximum peak intensity phi angles is less than the threshold.

9. The method of claim 7, wherein setting the phi offset value further comprises:
  adjusting the phi offset value for the ultrasound scanner based on the determined difference, in response to determining that the difference between the first and second maximum peak intensity phi angles is greater than the threshold.

10. The method of claim 4, wherein setting the phi offset value for the ultrasound scanner comprises:
  determining whether the difference between the first and second maximum peak intensity phi angles is less than a threshold.

11. The method of claim 10, wherein setting the phi offset value further comprises:
  setting the phi offset value for the ultrasound scanner to a current phi offset value, in response to determining that the difference between the first and second maximum peak intensity phi angles is less than the threshold.

12. The method of claim 10, wherein setting the phi offset value further comprises:
  adjusting the phi offset value for the ultrasound scanner based on the determined difference, in response to determining that the difference between the first and second maximum peak intensity phi angles is greater than the threshold.

13. A system, comprising:
  an ultrasound probe including:
    a transducer configured to rotate about a theta axis and a phi axis, wherein the phi axis is perpendicular to the theta axis; and
  a processing device configured to:
    collect, from a reflective planar target, first ultrasound data in a scan plane by rotating the transducer about the phi axis,
    calculate a first maximum peak intensity phi angle from the first ultrasound data,
    rotate the transducer 180° about the theta axis,
    collect, from the reflective planar target, second ultrasound data in the scan plane by rotating the transducer about the phi axis,
    calculate a second maximum peak intensity phi angle from the second ultrasound data,
    determine a difference between the first and second maximum peak intensity phi angles, and
    set a phi offset value for the ultrasound probe based on the determined difference.

14. The system of claim 13, wherein when setting the phi offset value for the ultrasound probe, the processing device is configured to:
  determine whether the difference between the first and second maximum peak intensity phi angles is less than a threshold.

15. The system of claim 14, wherein the setting the phi offset value, the processing device is further configured to:
  set the phi offset value for the ultrasound probe to a current phi offset value, in response to determining that the difference between the first and second maximum peak intensity phi angles is less than threshold.

16. The system of claim 14, wherein when setting the phi offset value, the processing device is further configured to:
adjust the phi offset value for the ultrasound probe based on the determined difference, in response to determining that the difference between the first and second maximum peak intensity phi angles is greater than the threshold.

* * * * *